United States Patent [19]

Nioue et al.

[11] Patent Number: 4,900,725
[45] Date of Patent: Feb. 13, 1990

[54] STEROIDS INCLUDING A SPIRO RING IN POSITION 17, THE PROCESS FOR THEIR PREPARATION AND THEIR USE

[75] Inventors: Francois Nioue, Les Pavillons sous Bois; Lucien Nedelec, Le Raincy; Daniel Philibert, LaVarenne Saint Hilaire; Martine Moguilewsky, Paris, all of France

[73] Assignee: Roussel Uclaf, Paris, France

[21] Appl. No.: 138,847

[22] PCT Filed: Mar. 26, 1987

[86] PCT No.: PCT/FR87/00096
§ 371 Date: Nov. 25, 1987
§ 102(e) Date: Nov. 25, 1987

[87] PCT Pub. No.: WO87/05908
PCT Pub. Date: Oct. 8, 1987

[30] Foreign Application Priority Data

Mar. 26, 1986 [FR] France .............................. 86 04355

[51] Int. Cl.$^4$ ..................... A61K 31/58; C07D 311/96
[52] U.S. Cl. ........................................ 514/173; 540/6; 514/843

[58] Field of Search ................. 549/331; 514/173, 843; 540/6

[56] References Cited

U.S. PATENT DOCUMENTS

| 3,509,135 | 4/1970 | Brown ................................... 540/23 |
| 3,764,596 | 10/1973 | Galantay .............................. 514/874 |
| 4,396,614 | 8/1983 | Nedelec et al. ...................... 514/173 |

FOREIGN PATENT DOCUMENTS 0097572 1/1984 European Pat. Off. .

Primary Examiner—H. M. S. Sneed
Assistant Examiner—James A. Saba
Attorney, Agent, or Firm—Bierman and Muserlian

[57] ABSTRACT

Products having the formula (I) wherein $R_1$ is an aryl or aralkyl, $R_2$ is a hydrocarbonated radical (1-18 carbon atoms), the dotted lines indicate an optional bond, the cycles A, B and C represent (II), (III), (IV), (V), (VI); R' and R'' are H, alkyl (1-4 carbon atoms). Re is H, alkyl (1-6 carbon atoms), acyl, and their salts, their preparation, their application as medicaments, the pharmaceutical compositions containing them and intermediaries.

19 Claims, No Drawings

STEROIDS INCLUDING A SPIRO RING IN POSITION 17, THE PROCESS FOR THEIR PREPARATION AND THEIR USE

The present invention is concerned with new steroids including a spiro ring in position 17, the process and the intermediates for their preparation, their use as medicaments and the pharmaceutical compositions containing them.

The subject of the invention is the products with the formula (I):

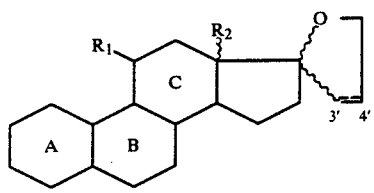

(I)

in which $R_1$ represents a carbocyclic or heterocyclic aryl or aralkyl radical possibly substituted, with the exception of an alkynyl phenyl radical possibly substituted, $R_2$ i alpha or beta position represents a hydrocarbon radical containing from 1 to 18 carbon atoms, the wavy line of the ether spiro indicates that the oxygen atom can be in alpha or beta position, the dotted line in position 3', 4' indicates the possible presence of a second bond between the carbons which carries it, the rings A and B having one of the following structures:

(a) either A and B represent the group:

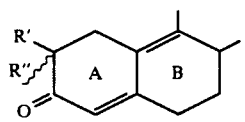

in which R' and R'', being identical or different, represent a hydrogen atom or an alkyl radical having from 1 to 4 carbon atoms:

(b) either A and B represent the group:

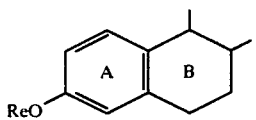

in which Re represents a hydrogen atom, an alkyl radical having from 1 to 6 carbon atoms, possibly substituted, or an acyl radical:

(c) or A, B and C represent the group:

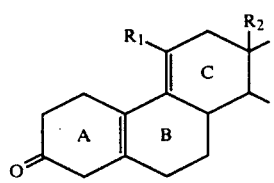

(d) or A and B represent the group:

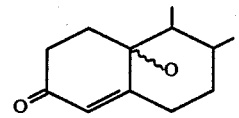

(e) or A and B represent the group:

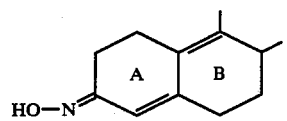

as well as their salts.

Among the products with the formula (I), the subject of the invention is particularly the products answering to the formula (I'):

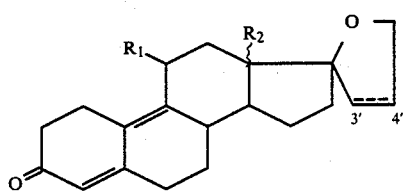

(I')

in which $R_1$ represents a carbocyclic or heterocyclic aryl or aralkyl radical, possibly substituted, with the exception of a phenyl alkynyl radical possibly substituted, $R_2$ in position alpha or beta represents a hydrocarbon radical containing from 1 to 18 carbon atoms, the oxygen atom of the ether spiro is in position beta, the dotted line in position 3', 4' indicates the possible presence of a second bond between the carbons which carries it, as well as their salts.

When $R_1$ represents a carbocyclic aryl or aralkyl radical, possibly substituted, it is preferred to be a phenyl or benzyl radical. These aromatic radicals can be substituted in ortho, meta or para by one or more alkyl radicals containing preferably from 1 to 8 carbon atoms: by one or more alkoxy radicals having preferentially from 1 to 8 carbon atoms such as the following radicals: methoxy, ethoxy, propyloxy, isopropyloxy, butyloxy, isobutyloxy, tert-butyloxy: alkenyloxy such as vinyloxy or allyloxy, all these radicals possibly being substituted: by one or more halogen atoms, such as fluorine, chlorine, bromine or iodine, preferably chlorine or fluorine: by one or more radicals chosen from the hydroxyl, trifluoromethyl, acyl having from 1 to 6 carbon atoms such as acetyl, propionyl, carboxy possibly esterified such as methoxycarbonyl, ethoxycarbonyl, propoxycarbonyl, alkylthio having from 1 to 8 carbon atoms such as methylthio, ethylthio possibly oxidized in the form of sulphoxide or sulphone: by one or more amino or amino mono- or disubstituted by alkyl radicals containing from 1 to 8 carbon atoms, themselves possibly substituted such as methylamino, dimethylamino and bis(chloroethyl)amino, amino or mono- or disubstituted amino radicals, possibly oxidized in N-oxide, the amino radicals incorporated in a heterocycle possibly containing a heteroatom chosen from the group formed by oxygen, nitrogen and sulphur, such as morpholino or piperidinyl radicals; naturally, the aryl or aralkyl radicals can be substituted by a combination of these different radicals, such as, for example, 2- methylthioethoxy, 3-fluoro, 4-dimethylamino: $R_1$ can also represent a heterocyclic aryl radical, possibly substituted by the different radicals considered above. There can be cited thienyl, furyl, isothienyl, isofuryl, thiazolyl, isothiazolyl, oxazolyl, isoxazolyl, thiadiazolyl, pyridinyl or piperidinyl radicals and the heterocycles known to an expert.

As substituent on the aryl nucleus, there can also be considered an alkyl amino (substituted) radical, such as the dimethylamino methyl, dimethylamino ethyl, methyl(dimethylaminoethyl)amino: an alkyloxy amino (substituted) radical such as the dimethylamino ethyloxy radical.

There can also be cited the radicals containing a silicium atom such as the trimethylsilyl phenyl radical.

The radicals previously cited containing a nitrogen or a sulphur atom can be oxidized.

In a general way, the products are preferred in which the substituent $R_1$ includes a heteroatom, preferably nitrogen or sulphur.

Among the different $R_1$ radicals, the following can be cited:

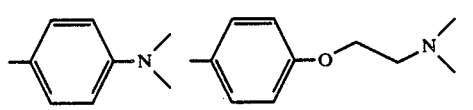

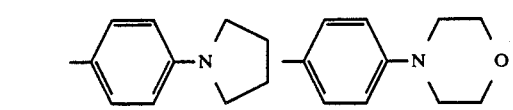

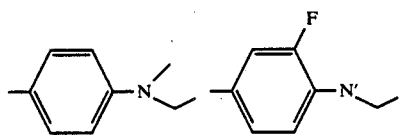

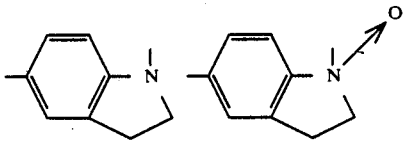

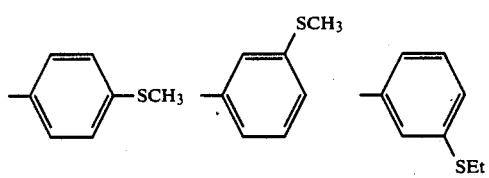

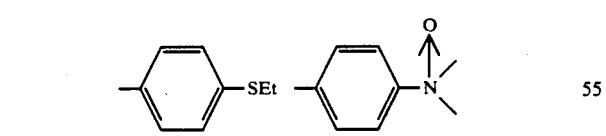

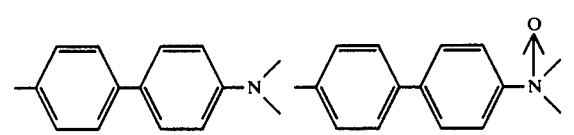

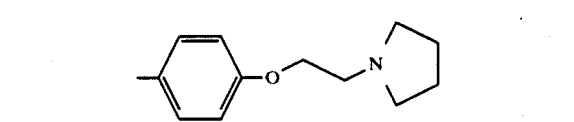

-continued

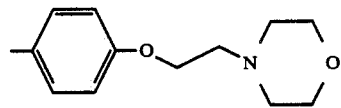

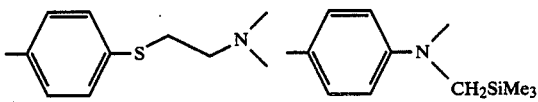

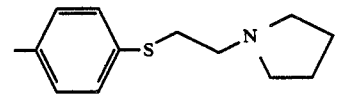

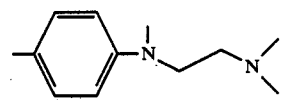

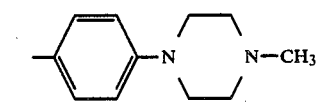

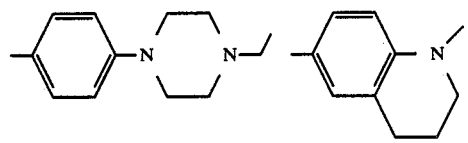

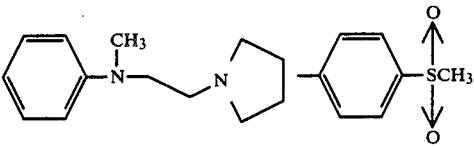

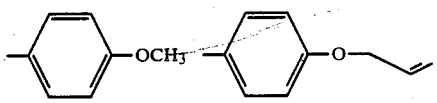

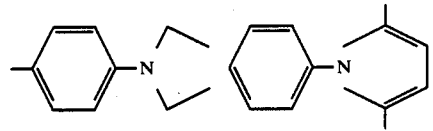

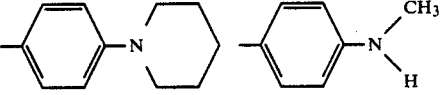

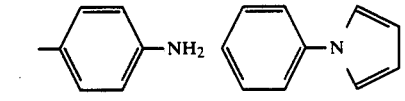

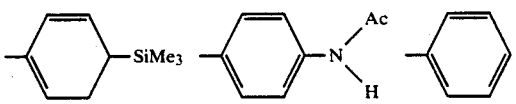

The radical $R_2$ preferably represents a linear or branched saturated alkyl radical, containing from 1 to 4 carbon atoms, for example a methyl, ethyl, propyl or butyl radical.

Preferably $R_2$ represents a methyl or ethyl radical. More preferably, $R_2$ represents a methyl radical.

The radical $R_2$ can be in alpha or beta position. The products are preferred in which $R_2$ is in beta position.

When $R_1$ includes a carboxy function, the latter can be salified. Among the possible salts, there can be cited, for example, the salts of sodium, potassium, lithium, calcium, magnesium or ammonium. Among the organic bases, there can be cited methylamine, propylamine, trimethylamine, diethylamine, triethylamine, N,N-dimethylethanolamine, tris(hydroxymethyl)aminomethane, ethanolamine, pyridine, picoline, dicyclohexylamine, morpholine, benzylamine, procaine, lysine, arginine, histidine, and N-methylglucamine.

When $R_1$ includes a function salifiable by an acid and particularly an amino function, addition salts are obtained with acids.

The invention is naturally extended to the addition salts with acids of the salifiable compounds with the formula (I), such, for example, as the salts formed with the following acids: hydrochloric, hydrobromic, nitric, sulphuric, phosphoric, acetic, formic, propionic, benzoic, maleic, fumaric, succinic, tartaric, citric, oxalic, glyoxylic, aspartic, alkane sulphonic such as methane- or ethane-sulphonic acids, arysulphonic such as benzene- or paratoluene-sulphonic acids and aryl carboxylic.

Among the products with the formula (I), the products are preferred in which the oxygen atom of the spiro-ether is in position 17 beta and the rings A and B represent the group:

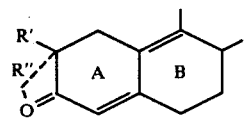

in which R' and R" represent a hydrogen atom.

Among the products with the formula (I), the products are preferred in which $R_1$ represents either an aryl or an aralkyl radical carrying an amine function

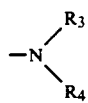

in which $R_3$ and $R_4$ each represent a primary, secondary or tertiary alkyl radical containing from 1 to 8 carbon atoms, or $R_3$ and $R_4$ form, with the nitrogen atom to which they are bonded, a heterocycle possibly including a further heteroatom chosen from the group formed by oxygen, nitrogen, sulphur and silicium, or an aryl radical carrying a methylthio or ethylthio function, as well as their salts.

$R_3$ and $R_4$ can be identical or different and represent in particular the values methyl, ethyl, propyl, isopropyl, butyl or tert-butyl, or $R_3$ and $R_4$ can in particular represent, with the atom that carries them, morpholinyl, imidazolidinyl, pyrrolidinyl, piperidinyl or piperazinyl radicals.

There are equally regarded in particular the products with the formula (I) in which the aryl radical is a phenyl radical and the substituent carried by the phenyl radical is in para position, as well as their salts.

Among the values for $R_1$, the following are preferred:

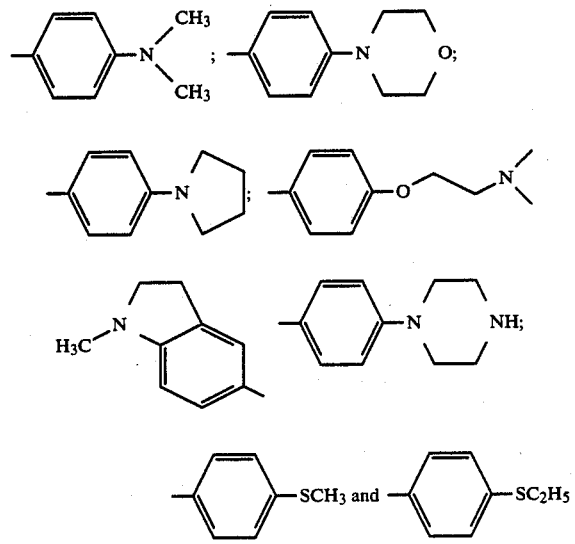

and more particularly still, the values:

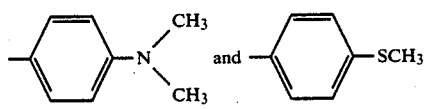

Among the products with the formula (I), those are preferred in which the substituent $R_2$ represents a methyl radical in alpha or beta position, or an ethyl radical in beta position.

The invention has more particularly as its subject the products described further on in the examples, of which the names follow:

(17 R) 4',5'-dihydro-11-beta-[4-(dimethylamino)-phenyl]- spiro(estra-4,9-dien-17,2'(3H)-furan)-3- one, (17 R) 11-beta-[4-dimethylamino)phenyl]-spiro(estra-4,9-dien-17,2'-(5H)-furan)-3-one, (17 R) 11-beta-[4-(methylthio)phenyl]-spiro(estra-4,9-dien17,2'-(5H)-furan)-3-one, (17 R) 4',5'-dihydro-11beta-[4-(methylthio)phenyl]-spiro(estra-4,9-dien-17,2'(5H)-furan)-3one, (17 R) 11-beta-[4-(1-pyrrolidinyl)pheny]-spiro(estra-4,9-dien-17,2'-(5H)-furan)-3-one, (17 R) 4',5'-dihydro-11beta-[4-(1-pyrrolidinyl)phenyl]-spiro(estra-4,9-dien-17,2'-(3H)-furan-3-one, (17 R) 4',5'-dihydro-11-beta-[4-(2,3-dihydro-1-methyl)(1H)-indol-5-yl]-spiro(estra-4,9-dien-17,2'-3H)-furan)3-one, (17 R) 11-beta-[4-(ethylthio)phenyl]-spiro(estra-4,9-dien-17,2'-(5H)-furan)-3-one, as well as their salts.

The invention also has as its subject a process for the preparation of the products with the formula (I) as defined above, characterized in that:

(a) to prepare the products with the formula ($I_4$:

(b) to prepare the products with the formula (I_B):

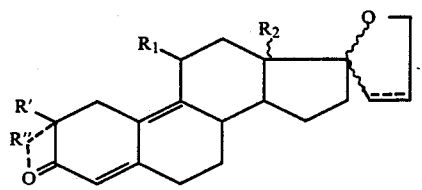
(I_A)

in which $R_1$ and $R_2$ retain the same significance as before and R' and R" each represent a hydrogen atom or an alkyl radical or else one represents a hydrogen atom and the other represents an alkyl radical, either a product with the formula (II):

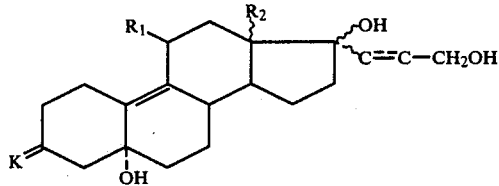
(II)

or a product with the formula (III):

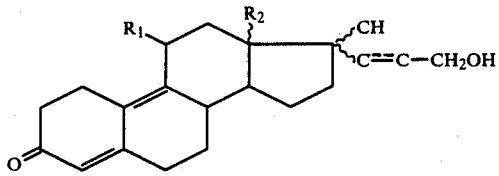
(III)

in which products $R_1$ and $R_2$ have the previously indicated significance and K represents a protector group of the ketone radical, is submitted to the action of a cyclization reagent in order to obtain respectively, either the products with the formula (IV):

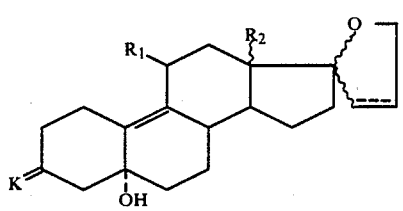
(IV)

which product with the formula (IV) are submitted to the action of a dehydration reagent also able to liberate the ketone function in order to obtain the products with the formula (I_A) in which R' and R" represent a hydrogen atom, or the said products with the formula (I_A) and which, if desired, are submitted to an oxidation of the products with the formula (I_A) in which $R_1$ includes a sulphur or nitrogen atom, in order to obtain the products in which $R_1$ includes a sulphur atom oxidized into sulphoxide or sulphone or a nitrogen atom oxidized into N-oxide and which, if desired, the products with the formula (I_A are submitted to salification, or, if desired, the products with the formula (I_A) are submitted to the action of a strong base and then of an alkyl halogenide in order to obtain a product with the formula (I_A in which R' and/or R" represent an alkyl radical having from 1 to 4 carbon atoms;

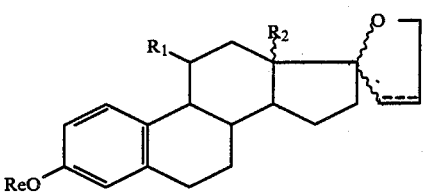
(I_B)

in which $R_1$, $R_2$ and Re retain the same significance as above, a product with the formula (I'_A):

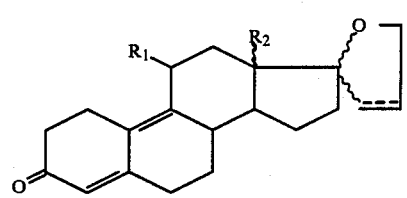
(I')_A in which $R_1$ and $R_2$ have the previously indicated significance, is submitted to the action of an aromatization agent, then, if required, to the action of a saponification agent and finally, if desired, submit the product with the formula (I_B) in which Re is a hydrogen atom to an alkylation or acylation reagent:

(c) to prepare products with the formula (I_C):

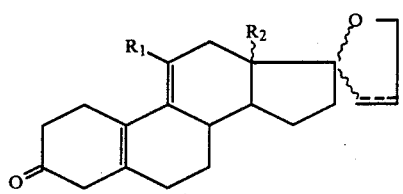

in which $R_1$ and $R_2$ retain the same significance as before, either a product with the formula (V):

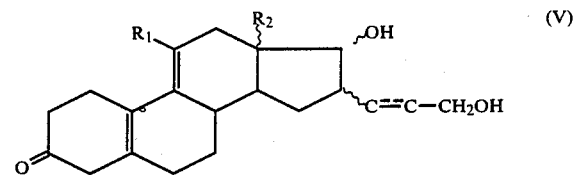
(V)

is submitted to the action of a cyclization agent, or a product with the formula (I'_A) is submitted to the action of an acylation agent and then to saponification;

(d) in order to prepare the products with the formula (I_D):

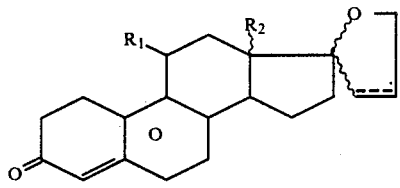
(I_D)

in which $R_1$ and $R_2$ retain the same significance as above, a product with the formula (I'_A) is submitted to the action of an epoxidation agent;

(e) in order to prepare the products with the formula (I$_E$):

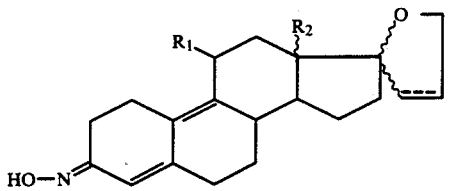

in which R$_1$ and R$_2$ retain the same significance as above, hydroxyllamine is made to act on a product with the formula (I'$_A$).

The invention also has as its subject a process for the preparation of the products with the formula (I) in which R$_1$ represents an aryl or aralkyl radical substituted by a carboxy radical, possibly esterified or salified, characterized in that a product with the formula (I$_F$):

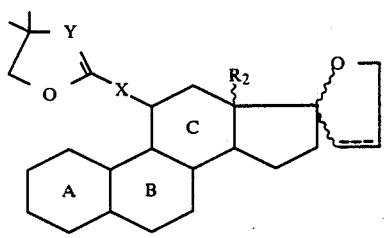

in which A, B, C and R$_2$ have the significance already indicated and X represents a carbocyclic or heterocyclic aryl or aralkyl radical, is submitted to an acid hydrolysis in order to obtain a product with the formula (I$_G$):

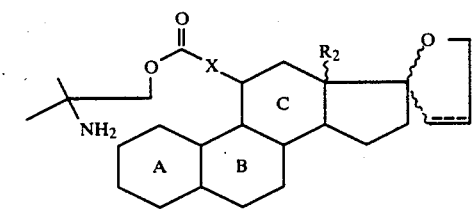

which, if required, is submitted to the action of a basic agent in order to obtain a product with the formula (I$_H$):

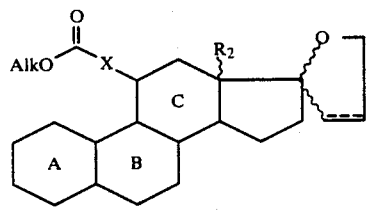

in which alk represents an alkyl radical having from 1 to 6 carbon atoms, which, if required, is saponified in order to obtain a product with the formula (I$_J$):

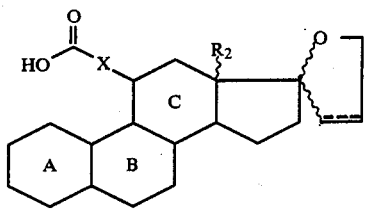

which, if required, is esterified or salified.

In a preferred way of carrying out the processes described above, the cyclization reagent which is preferably made to act on the products with the formulae (II), (III) or (V) is tosyl chloride in the presence of pyridine; methylsulphonyl chloride can also be used.

The conversion of the products with the formula (IV) by means of a dehydration reagent also able to liberate the ketone function, is preferably carried out by means of a sulphonic resin (acid form), for example, a commercial sulphonic resin with a polystyrene support or with a styrene/divinyl/benzene polymer support. There can, however, also be used a mineral acid, such as hydrochloric acid or sulphuric acid in a lower alkanol or perchloric acid in acetic acid or a sulphonic acid such as paratoluene sulphonic acid.

The oxidation agent which is made to act on the products with the formula (I$_A$) or the epoxidation agent which is made to act in order to obtain the products with the formula (I$_D$) is preferably a peracid such as metachloroperbenzoic acid, peracetic acid or perphthalic acid. There can also be used hydrogen peroxide alone or in the presence of hexachloro- or hexafluoroacetone.

Naturally, according to the number of functions which may be the subject of an oxidation, one or more equivalents of the oxidizing agent can be used.

Thus, for example, if it is desired to oxidize the sulphur atom carried by R$_1$ into sulphone, naturally at least two equivalents of the oxidizing agent must be used.

The strong base which is used on the products with the formula (I$_A$) can be an alkali metal amide, such as sodium or lithium amide, possibly prepared in situ;

the alkyl halogenide which is used is preferably an iodide such as methyl iodide;

the aromatizing agent used to prepare the products with the formula (I$_B$) is preferably an acyl halogenide such as acetyl bromide or an acid anhydride such as acetic anhydride or a mixture of the two;

the possible acylation of the products with the formula (I$_B$) and the acylation leading to the products with the formula (I$_B$) is carried out according to the usual methods. For example, an alkyl halogenide is used;

the saponifying agent used to obtain the products with the formulae (I$_B$), (I$_C$) or (I$_J$) is preferably an alkaline base such as sodium or potassium and the reaction is carried out in a lower alcohol such as methanol or ethanol;

the oximation of the products with the formula (I'$_A$) is carried out by using hydroxylamine in the form of a salt, preferably the hydrochloride in an alcohol at the temperature reflux;

the acid hydrolysis to which the products with the formula (I$_F$) are submitted is carried out according to the usual conditions; for example, a mineral acid, preferably hydrochloric acid, can be used in aqueous solution;

the basic agent used to obtain the products (I$_H$) is preferably an alkaline alcoholate such as sodium ethylate.

The salification is carried out in the usual conditions. For example, the operation can be done in the presence of sodium hydroxide in ethanol. There can also be used a sodium salt such as the carbonate or the acid carbonate of sodium or potassium.

Similarly, the salification by an acid is carried out in the usual conditions. It is preferred to operate with hydrochloric acid, for example, in an ethereal solution.

The products with the formula (I) as well as their pharmaceutically acceptable salts, are particularly interesting products from the pharmaceutical view point.

Studying the products on the hormone receptors has enabled progestomimetic or anti-progestomimetic, androgenic or anti-androgenic activities to be shown.

The products with the formula (I) possess in particular a remarkable anti-pregestomimetic activity.

The products with the formula (I) also possess an anti-glucocorticoid activity, as is shown by the results of the tests described later on.

Certain products, however, show an anti-progestomimetic activity greater than their anti-glucocorticoid property.

The products with the formula (I) as well as their pharmaceutically acceptable salts which possess anti-progestomimetic properties can be used as contraceptives; they can be used against hormone irregularities.

Certain products with the formula (I) as well as their pharmaceutically acceptable salts can also offer progestomimetic properties and can thus be used in the treatment of amenorrhoea, dysmenorrhea and luteal deficiencies.

These products with the formula (I) as well as their pharmaceutically acceptable salts, can therefore be used as medicaments principally to combat secondary effects of the glucocorticoids; they also enable troubles due to a hypersecretion of the glucocorticoids to be combatted and notably enable aging in general and more particularly hypertension, athero- sclerosis, osteoporosis, diabetes, obesity as well as immuno-depression and insomnia to be combatted.

The products with the formula (I) as well as their pharmaceutically acceptable salts which offer anti-androgenic properties can be used in the treatment of hypertrophies and of cancer of the prostate, of hyperandrogenia, anaemia, hirsutism and acne.

The products with the formula (I) as well as their pharmaceutically acceptable salts also possess anti-proliferative properties which makes them utilisable in the treatment of hormone-dependent cancers, notably mammary carcinomas and their metastases. These properties make them utilisable in the treatment of benign tumors.

Certain of the products with the formula (I) as well as their pharmaceutically acceptable salts possess estrogenic and/or anti-estrogenic properties. The anti-estrogenic properties make them utilisable in the treatment of estrogenic dependent cancers.

The estrogenic properties which the said products with the formula (I) as well as their pharmaceutically acceptable salts can also offer make them utilisable also in the treatment of troubles connected with hypofollicullinia, for example, amenorrhoea, dysmenorrhoea, repeated abortions, premenstrual troubles, as well as the treatment of the menopause.

Therefore, the invention has as its subject as medicaments the pharmaceutically acceptable products with the formula (I), i.e., those which are non-toxic at the doses used, as well as their pharmaceutically acceptable salts.

The invention has particularly as its subject, as medicaments, the preferred products with the formula (I) mentioned above, and quite particularly the products of which the names follow:

(17 R) 4',5'-dihydro-11-beta-[4-(dimethylamino)-phenyl]-spiro(estra-4,9-dien-17,2'(3H)-furan-3-one, (17 R) 11-beta-[4-dimethylamino)phenyl]-spiro(estra-4,9-dien-17,2'-(5H)-furan)-3-one, (17 R) 11-beta-[4-(methylthio]-spiro(estra-4,9-dien-17,2'-(5H)-furan-3-one, (17 R) 4',5'-dihydro-11-beta-[4-(methylthio)phenyl]-spiro(estra-4,9-dien-17,2'(5H)-furan)-3-one, (17 R) 11-beta-[4-(1-pyrrolidinyl)phenyl]-spiro(estra-4,9-dien-17,2'-(5)-furan)-3-one, (17 R) 4',5'-dihydro-11-beta-[4-(1-pyrrolidinyl)phenyl]-spiro(estra-4,9-dien-17,2'-(3H-furan)-3-one, (17 R) 4',5'-dihydro-11-beta-[4-(2,3-dihydro-1-methyl)-(1H)-indol-5-yl]-spiro(estra-4,9-dien-17,2'-(3H)-furan)-3-one, (17 R) 11-beta-[4-(ethylthio)phenyl]-spiro(estra-4,9-dien-17,2'-(5H)-furan)-3-one, as well as their pharmaceutically acceptable salts.

The useful posology varies as a function of the affection to be treated and of the administration route; it can vary, for example, from 10 mg to 1 g per day in an adult by oral route.

The new products with the formula (I), and their salts, as defined above, can be employed to prepare pharmaceutical compositions containing, as active principle, one at least of the said products.

The products with the formula (I) and their salts are used by digestive, parenteral or local route. They can be prescribed in the form of plain or sugar-coated tablets, capsules, granules, suppositories and injectable preparations, ointments, creams and gels, which are prepared according to the usual methods.

The active principle or principles can be incorporated with the excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, the various wetting, dispersing or emulsifying agents and preservatives.

The invention therefore has as subject the pharmaceutical compositions containing as active principle at least one product with the formula (I), or at least one of their pharmaceutically acceptable salts.

The products with the formulae (II), (III) and (V) are known or can be prepared by the usual methods such as those described in the European patent EP No. 0,147,361.

The products with the formulae (II), (III) and (V) in which the oxygen atom of the spiroether is in the alpha position can be prepared according to the method indicated in the European patent EP No. 0,129,499.

The invention also has as its subject as new industrial products, the products with the formula (IV):

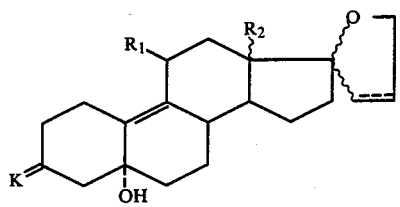

(IV)

in which R₁, R₂ and K retain the same significance as previously.

In addition to the following examples, which illustrate the invention without, however, limiting it, the following products constitute products which can be obtained within the scope of the present invention.

The products with the formula (I):

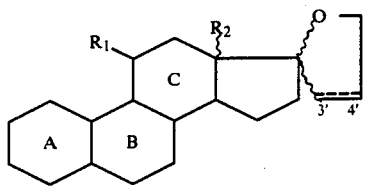

in which A, B, C have the values previously indicated and R₁, R₂ and the bond 3'-4' have the following values:

| R₁ | R₂ | 3' 4' |
|---|---|---|
| phenyl | βCH₃ | C—C |
| " | " | C=C |
| 4-CH₃-phenyl | " | C—C |
| " | " | C=C |
| 3-CH₃-phenyl | " | C—C |
| " | " | C=C |
| 2-CH₃-phenyl | " | C—C |
| " | " | C=C |
| 4-Cl-phenyl | " | C—C |
| " | " | C=C |
| 3-Cl-phenyl | " | C—C |
| " | " | C=C |
| 2-Cl-phenyl | " | C—C |
| " | " | C=C |
| 4-NH₂-phenyl | " | C—C |
| 4-NH₂-phenyl | β CH₃ | C=C |
| 3-NH₂-phenyl | " | " |
| " | " | C=C |
| 4-N(CH₃)₂-phenyl | β C₂H₅ | C—C |
| " | " | C=C |
| " | α CH₃ | C—C |
| " | " | C=C |
| 3-NHCH₃-phenyl | β CH₃ | C—C |
| " | " | C=C |

-continued

| R₁ | R₂ | 3' 4' |
|---|---|---|
| *p*-OCH₃-C₆H₄- | " | C—C |
| " | " | C=C |
| *p*-OCH(CH₃)₂-O-C₆H₄- | " | C—C |
| " | " | C=C |
| *m*-OCH₃-C₆H₄- | " | C—C |
| " | " | C=C |
| *p*-(CH₃)₂NCH₂CH₂O-C₆H₄- | " | C—C |
| " | " | C=C |
| *p*-(pyrrolidinyl-CH₂CH₂-O)-C₆H₄- | β CH₃ | C—C |
| " | " | C=C |
| *p*-NHCH₃-C₆H₄- | " | C—C |
| " | " | C=C |
| *p*-NHCOCH₃-C₆H₄- | " | C—C |
| " | " | C=C |

-continued

| R₁ | R₂ | 3' 4' |
|---|---|---|
| *p*-(CH₃)₂N(→O)-C₆H₄- | " | C—C |
| " | " | C=C |
| *p*-(pyrrolidinyl)-C₆H₄- | " | C—C |
| " | " | C=C |
| *p*-SEt-C₆H₄- | " | C—C |
| " | " | C=C |
| *m*-SEt-C₆H₄- | " | C—C |
| " | " | C=C |
| *p*-CH₃S(→O)-C₆H₄- | " | C—C |
| " | " | C=C |
| *p*-CH₃N(CH₂CH₂S)-C₆H₄- | " | C—C |
| " | " | C=C |
| *m*-SCH₃-C₆H₄- | β CH₃ | C—C |
| " | " | C=C |

-continued
| R₁ | R₂ | 3' 4' |
|---|---|---|
| 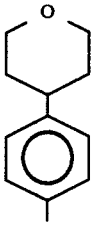 | " | C—C |
| " | " | C=C |
| " | " | C—C |
| 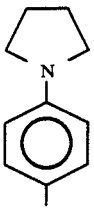 | " | |
| " | " | C=C |
| " | " | C—C |
| 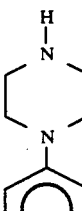 | " | |
| " | " | C=C |
| " | " | C—C |
| 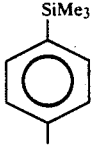 | " | |
| " | " | C=C |
| " | " | C—C |
| 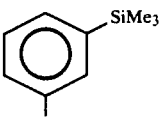 | " | |
| " | " | C=C |
-continued
| R₁ | R₂ | 3' 4' |
|---|---|---|
| 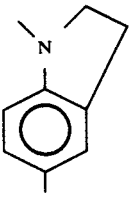 | " | C—C |
| " | " | C=C |
| " | " | C—C |
|  | " | |
| " | " | C=C |
| " | " | " |
|  | | |
| 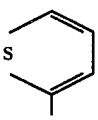 | β CH₃ | C—C |
| " | " | C=C |
| " | " | C—C |
| 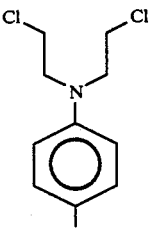 | | |
| " | " | C=C |
| " | " | C—C |
| 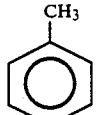 | | |
| " | " | C=C |
| " | " | C—C |
| 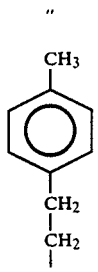 | | |

-continued

| R₁ | R₂ | 3' 4' |
|---|---|---|
| " | " | C=C |

EXAMPLE 1

(17 R)
4'5'-dihydro-11-beta-[4-(dimethylamino)phenyl]-spiro(estra-4,9-dien-17,2'-(3H))-furan)-3-one Stage A: gamma-lactone of 5-alpha,17-beta-dihydroxy-11-beta-[4-dimethylamino)-phenyl]-3,3-[(1,2-ethanediyl)bisoxy]-19-nor-17-alpha-pregn-9-en-21-carboxylic acid 60 cm³ of tetrahydrofuran is introduced at −70° C. into 60 cm³ of a 15% solution of butyllithium in hexane (1.6M), then, at −60° C., 9.2 cm³ of N,N,N',N'-tetramethylphosphoramidate of allyl in solution in 30 cm³ of tetrahydrofuran is introduced drop by drop. After agitating for 45 minutes at −10° C., 9.95 g of 3,3-(1,2-ethanediyl) cyclic acetal of 11-beta-[4-(dimethylamino)-phenyl]-5-alpha-hydroxyphenyl]estr-9-en-3,17-dione in solution in 20 cm³ of tetrahydrofuran is added: a further 20 cm³ of tetrahydrofuran is added, with agitation for an hour at 20° C.

The reactional mixture is poured into an aqueous solution of ammonium chloride, extracted with ethyl acetate, washed with water, dried and concentrated to dryness by distilling under reduced pressure. The residue is chromatographed on silica, eluting with a mixture of cyclohexane and ethyl acetate (3/7), and 3.9 g of the crude product sought is obtained, which is dissolved in methylene chloride and filtered; isopropyl ether is added to the filtrate, the methylene chloride is eliminated by distilling, and after separating and washing, 3.45 g of the product sought is obtained. m.p. 198° C.

IR Spectrum (chloroform): OH combined 3610 cm⁻¹, gamma lactone 1760 cm⁻¹ ketal, aromatic bands 1610 cm⁻¹, 1516 cm⁻¹, 823 cm⁻¹.
Analysis: $C_{31}H_{41}O_5N$ (507.67):

|  | C % | H % | N % |
|---|---|---|---|
| Calculated | 73.34 | 8.14 | 2.76 |
| Found | 73.1 | 8.3 | 2.8 |

Stage B: (1,2-ethanediyl) cyclic acetal of 5-alpha,17-betadihydroxy-11-beta-[4-(dimethylamino)-phenyl]-17-alpha-(3-hydroxypropyl)estr-9-en-3-one 1.014 g of the product obtained above is dissolved in 30 cm³ of tetrahydrofuran, then, under a current of nitrogen and while agitating, 500 mg of lithium aluminium hydride is added by fractions; the temperature rises to 35° C., and after agitating for 1 hour 30 minutes at 20° C., ethyl acetate is added drop by drop, then a saturated aqueous solution of ammonium chloride is added; the supernatant organic phase is decanted, and the residue is extracted while agitating with a mixture of tetrahydrofuran and ethyl acetate (1/1). The organic phases are washed with salted water, then dried and concentrated to dryness by distilling under reduced pressure, and 993 mg of the crude product sought is obtained (m.p. 210° C.), used as it is for the following stage.

The analytical sample obtained after purification by chromatography on silica, eluting with a mixture of ethyl acetate and ethanol (95/5), then crystallization from ethanol, melts at 234° C.

IR Spetrum (chloroform): OH at 3620 cm⁻¹ and OH combined. Aromatic bands at 1613 cm⁻¹, 1560 cm⁻¹, 1517 ⁻¹, presence of ketal.
Analysis $C_{31}H_{45}O_5N$, 511.7:

|  | C % | H % | N % |
|---|---|---|---|
| Calculated | 72.76 | 8.86 | 2.73 |
| Found | 72.6 | 9.0 | 2.7 |

Stage C: Mixture of (1,2-ethanediyl) cyclic acetal of (17 R) 4',5'-dihydro-11-beta-[4-dimethylamino)phenyl]-5-alpha-hydroxy-spiro(estr-9-en-17,2'-(3H)-furan)-3-one (compound A) and of (17 R) 4',5'-hydro-11-beta-[4-(dimethylamino)phenyl]-spiro(estra-4,9-dien-17,2'-(3H)-furan)-3-one (compound B)

2 g of the above compound is dissolved in 30 cm³ of pyridine, then, at +3° C., 1.52 g of tosyl chloride is added, and the mixture is left for 40 minutes at 20° C. The reactional medium is then cooled to +3° C., water and then a solution of sodium biocarbonate are added, followed by extraction with ethyl acetate, washing with water, drying and concentrating to dryness by distilling under reduced pressure. The pyridine is eliminated by azeotropic entrainment with toluene, the residue is chromatographed on silica, eluting with a mixture of cyclohexane and ethyl acetate (7/3), and 395 mg of compound (B) and 500 mg of compound (A) are obtained.

Check of compound A:
IR Spectrum (chloroform): absence of band CO, 5OH 3512 cm⁻¹, aromatics 1613 cm⁻¹, 1557 cm⁻¹, 1617 cm⁻¹.

Stage D: (17 R)
4',5'-dihydro-11-beta-[4-(dimethylamino)phenyl]-spiro(estra-4,9-dien-17,2'-(3H)-furan)-3-one (compound B)

The 500 mg of compound A obtained at stage C is dissolved in 15 cm³ of ethanol, 10 cm³ of a 2N aqueous solution of hydrochloric acid is added, and the mixture is left for 45 minutes at 20° C. After adding an aqueous solution of sodium bicarbonate, extracting with methylene chloride, washing, drying and concentrating to dryness by distilling under reduced pressure, 390 mg of crude compound B is obtained.

Purification of compound B

The 395 mg of compound B obtained at stage C and the 390 mg of compound B obtained above are put together, and chromatographed on silica, eluting with a mixture of cyclohexane and ethyl acetate (7/3); 645 mg of compound B is obtained.

After recrystallizing from aqueous ethanol, 367 mg of the expected product is obtained, m.p. 100° C. (not very pure).

Compound B:
IR Spectrum (chloroform): absence of OH; ketone at position 3, 1653 cm⁻¹, C=C, aromatic 1612 cm⁻¹, 1597 cm⁻¹, 1518 cm⁻¹.

UV Spectrum: in ethanol: max. 260 nm $\epsilon=18,900$, max. 302 nm $\epsilon=22.100$; in ethanol HCl 0.1 N: max. 300 nm $\epsilon=20,500$, inflexions 240, 249, 270 nm.

Analysis: $C_{29}H_{37}NO_2$ 431.62:

|            | C %  | H %  | N %  |
|------------|------|------|------|
| Calculated | 80.7 | 8.64 | 3.24 |
| Found      | 80.6 | 8.8  | 3.2  |

NMR Spectrum deuterochloroform): Peak at 0.59 ppm, hydrogens of the methyl 18; Peak at 2.30 ppm, hydrogens of the dimethylamino; Peaks at 3.76 ppm, hydrogen of $CH_2O$; Peaks at 4.3 ppm, hydrogen in position 11; Peak at 5.70 ppm, hydrogen in position 4; Peaks at 6.64 and 7.03 ppm, aromatic hydrogens.

EXAMPLE 2

(17 R) 11-beta-[4-(dimethylamino)phenyl]-spiro (estra-4,9-dien-17,27-(5H)-furan)-3-one 1.425 g of (Z) 11-beta-[4-dimethylamino)phenyl]-17-beta-hydroxy-17-alpha-(3-hydroxy-1-propenyl)estra-4,9-dien-3-one is dissolved in 30 cm³ of pyridine, and at +3° C., 3 g of tosyl chloride is added, with agitation for 4 hours at 20° C. After cooling to +3° C., water is added, with agitation for 15 minutes, followed by extraction with ethyl acetate, washing with water, drying and concentrating to dryness by distilling under reduced pressure. Azeotropic entrainment is done with toluene to eliminate all the pyridine, then the residue is dissolved in ethyl ether, filtered and concentrated to dryness, and 1.37 g of the product sought is obtained, crystallized.

After re-crystallization from isopropyl ether, 1.23 g of the pure product sought is obtained.

Checks

IR Spectrum (chloroform):

| 3 keto   | delta⁴ | C = O | 1655 cm⁻¹ |
|----------|--------|-------|-----------|
|          |        | C = C | 1612 cm⁻¹ |
| aromatic |        |       | 1597 cm⁻¹, 1562 cm⁻¹, 1518 cm⁻¹ |

UV-Spectrum:

| Ethanol        | max. at 260 nm | E = 19,600 |
|----------------|----------------|------------|
|                | max. at 302 nm | E = 23,200 |
| Ethanol/HCl 0.1 N |             |            |
|                | infl. 215 nm   |            |
|                | infl. 238 nm   |            |
|                | max. 300 nm    | E = 21,600 |

Analysis: $C_{29}H_{35}NO_2$:

|            | C %   | H %  | N %  |
|------------|-------|------|------|
| Calculated | 81.08 | 8.21 | 3.26 |
| Found      | 81.0  | 8.3  | 3.3  |

NMR Spectrum (deuterochloroform): Peak at 0.62 ppm, hydrogen of the methyl 18; Peak at 2.92 ppm, hydrogen of the dimethylamino; Peaks at 4.29 ppm, hydrogen at position 11; Peak at 4.60 ppm, hydrogen of $CH_2O$; Peak at 5.78 ppm, hydrogen at position 4; Peak at 5.88 ppm, hydrogens in positions 3' and 4' Peaks at 6.69 ppm, and 7.05 ppm, aromatic hydrogens.

EXAMPLE 3

(17 R) 11-beta-[4-(methylthio)phenyl]-spiro(estra-4,9-dien-17,2'-(5H)-furan)-3-one Stage A: 3,3-(1,2-ethanediyl) cyclic acetal of 5-alpha,10-alphaepoxy, 17-beta-hydroxy-17-alpha-[3-(tetrahydro-2H-2-pyrannyloxy)-1-propynyl]estr-9(11)-en-3-one Under an inert atmosphere, 5.06 cm³ of reagent HC≡C—CH₂OTHP and 30 cm³ of tetrahydrofuran are mixed together and cooled to −5° C., then 20 cm³ of a 1.65M solution of butyllithium in hexane is added drop by drop, with agitation for 30 minutes at 0° C. Then, over about 40 minutes at 0° C., 6.6 g of 3,3-(1,2-ethanediyl) cyclic acetal of 5-alpha10-alpha-epoxy[estra-9(11)-en-3,17-dione in solution in 55 cm³ of tetrahydrofuran is introduced. After agitation for 16 hours at 20° C., the reactional mixture is poured into a 10% aqueous solution of ammonium chloride, extracted with ethyl acetate, washed with water, dried, and concentrated to dryness by distillation under reduced pressure. The residue obtained is chromatographed on silica, eluting with a mixture of cyclohexane and ethyl acetate (1/1), obtaining 8.3 g of the compound sought, utilized as it is for the following stage.

IR Spectrum (chloroform): Free OH at 3601 cm⁻¹+a little absorption of combined OH; C=C— at 1640 cm ⁻¹; presence of OTHP.

Stage B: 3,3-(1,2-ethanediyl)cyclic acetal of 5-alpha,17-beta-dihydroxy-11-beta-[4-(methylthio)-phenyl]-17-alpha-[3-(tetrahydro-2H-2-pyrannyloxy)-1-propynl]estra-9-en-3-one (1°) Preparation of the magnesium compound Under an inert atmosphere, 3 g of magnesium turnings and 3 cm³ of tetrahydrofuran are mixed together, taken to 45° C., and a few drops of the following solution are added: 20.2 g of parabromothioanisole in solution in 70 cm³ of tetrahydrofuran. After initiating the reaction, the introduction of this solution is continued in such a way as to keep the temperature at about 50° C.; heating is continued for a further hour at 50° C. after the end of the introduction.

A magnesium compound titrating 1.1 N is obtained.

(2°) Condensation

Under an inert atmosphere, 80 cm³ of the magnesium compound solution, 90 cm³ of tetrahydrofuran and 887 mg of cuprous chloride are mixed together, cooled to −15° C., then, over about 15 minutes, a solution of 12.2 g of 3,3-(1,2-ethanediyl) cyclic acetal of 5-alpha, 10-alpha-epoxy-17-beta-hydroxy-17-alpha-[3-(tetrahydro-2H-2-pyrannyloxy)-1-propynl]estr-9(11)-en-3-one in 25 cm³ tetrahydrofuran is introduced, with agitation for one hour at 0° C. The reactional mixture is then poured into a 10% aqueous solution of ammonium chloride, extracted with ethyl acetate, washed with water, dried, and concentrated to dryness by distilling under reduced pressure. The residue obtained is chromatographed on silica, eluting by a mixture of cyclohexane and ethyl acetate (1/1), obtaining 15 g of the crude compound sought. 11 g of the product is crystallized from ethanol with 50% of water, so obtaining 10.2 g of the product sought, m.p. 160° C.

Checks

IR Spectrum (chloroform): OH in 17 at 3600 cm$^{-1}$ (free)+combined in 5 at 3610 cm$^{-1}$ aromatics at 1596 cm$^{-1}$; 1556 cm$^{-1}$; 1492 cm$^{-1}$; presence of OTHP.

UV Spectrum (ethanol): Infl. 228 nm; max. 255 nm ($\epsilon$=15,000); Infl. 288 nm; Infl. 297 nm.

Stage C: (Z) 3,3-(1,2-ethanediyl) cyclic acetal of 5-alpha,17-beta-dihydroxy-11-beta-[4-(methylthio)-phenyl]-17-alpha-[3-(tetrahydro-2H-2-pyrannyloxy)-1-propenyl]estr-9-en-3-one.

594 mg of 3,3-(1,2-ethanediyl) cyclic acetal of 5-alpha,17-beta-dihydroxy-11-beta-[4-(methylthio)-phenyl]-17-alpha-[3-(tetrahydro-2H-2-pyrannyloxy)-1-propynyl]estr-9-en-3-one obtained above is dissolved in 20 cm³ of ethyl acetate, and 60 mg of palladium hydroxide at 10% on activated charcoal is added, with agitation under an atmosphere of hydrogen for 14 hours. The catalyst is filtered off, the remainder is concentrated to dryness by distilling under reduced pressure and the residue obtained is chromatographed on silica, eluting with a mixture of cyclohexane and ethyl acetate (1/1), so obtaining 151 mg of the compound sought.

Checks

IR Spectrum (chloroform): A little free OH; mainly, combined OH at 3500 cm$^{-1}$; shoulder at 3410 cm$^{-1}$; aromatics at 1557 cm$^{-1}$, 1492 cm$^{-1}$, 831 cm$^{-1}$: presence of OTHP.

NMR Spectrum (deuterochloroform): Peak at 0.53 ppm, hydrogen of the methyl at 18; Peak at 2.47 ppm, hydrogen of the methyl of —SCH$_3$; Peak at 4.77 ppm, ketal hydrogen of THP; Peaks from 5.6 to 5.84 ppm, ethylene hydrogens; Peaks from 3.44 to 4.5 ppm, hydrogen of CH$_2$O and with hydrogen at 11; Peak at 7.17 ppm, aromatic hydrogens.

Stage D: (Z) 17-beta-hydroxy-17-alpha-(3-hydroxy-1propenyl)-11-beta-[4-(methylthio) phenyl]estra-4,9-dien-3-one 2.42 g of (Z) 3,3-(1,2-ethanediyl) cyclic acetal of 5-alpha, 17-beta-dihydroxy-11-beta-[4-(methlthio)-phenyl]-17-alpha-[3-(tetrahydro-2H-2-pyrannyloxy)-1-propenyl]estr-9-en-3-one obtained above is dissolved in 44 cm³ of methanol, 20 cm³ of a 2N aqueous solution of hydrochloric acid is added with agitation under an inert atmosphere for 1 hour 30 minutes. After diluting with water, extraction is done with ethyl acetate. The extracts are dried and concentrated to dryness by distilling under reduced pressure. The residue obtained is chromatographed on silica, eluting with a mixture of cyclohexane and ethyl acetate (1/1), so obtaining:

904 mg of the expected compound, 567 mg of (Z) 17-beta-hydroxy-17-alpha-3-(tetrahydro-2H-2-pyrannyloxy)-1-propenyl-11-beta-[4-(methylthio)phenyl]estra-4,9-dien-3-one, which is put back to acid hydrolysis in the same conditions, and after chromatographic purification, 188 mg of the compound sought is obtained.

Checks

IR Spectrum (chloroform): OH at 3609 cm$^{-1}$+combined; dienone at 1653 cm$^{-1}$; 1601 cm$^{-1}$; aromatic at 1555 cm$^{-1}$ and 1493 cm$^{-1}$.

NMR Spectrum (deuterochloroform): Peak at 0.63 ppm, hydrogen of methyl 18; Peak at 2.47 ppm, hydrogen of the methyl of —SCH$_3$; Peak at 4.33 ppm, hydrogen in position 11; Peak at 4.39 ppm, hydrogens of the CH$_2$O; Peaks from 5.59 to 5.92 ppm, ethylene hydrogens, Peaks from 7.04 to 7.24 ppm, aromatic hydrogens.

Stage E: (17R) 11-beta-[4-(methylthio)phenyl]-spiro(estra-4,9-dien-17,2'-(5H)-furan)-3-one 11.04 g of (Z) 17-beta-hydroxy-17-alpha-(3-hydroxy-1-propenyl)-11-beta-[4-(methylthio) phenyl]estra-4,9-dien-3-one obtained previously is dissolved in 20 cm³ of pyridine, 2.1 g of tosyl chloride is added, with agitation for 2 hours at 20° C. After diluting with water and with ice, extraction is done with ethyl acetate. The extracts are washed with a dilute aqueous solution of hydrochloric acid, and with water, then dried and concentrated to dryness by distilling under reduced pressure. The residue obtained is chromatographed on silica, eluting with a mixture of cyclohexane and ethyl acetate (6/4), obtaining 820 mg of the crude product sought, which is crystallized from a mixture of methylene chloride and isopropyl ether, obtaining 694 mg of the product sought.

Checks

IR Spectrum (chloroform: absence of OH; dienone, 1653 cm$^{-1}$ and 1601 cm$^{-1}$; aromatics at 1555 cm$^{-1}$ and 1492 cm$^{-1}$.

NMR Spectrum (deuterochloroform): Peak at 0.59 ppm, hydrogens of the methyl at 18, Peak at 2.48 ppm, hydrogens of the methyl of —SCH$_3$; Peaks from 4.30 to 4.34 ppm, hydrogen in position 11; Peak at 4.6 ppm, hydrogens of the CH$_2$O; Peak at 5.81 ppm, hydrogen at position 4; Peak at 5.89 ppm, hydrogens in positions 3' and 4'; Peaks from 7.04 to 7.27 ppm, aromatic hydrogens.

UV Spectrum (crude formula):

| Max. at 260 nm. | E = 16,100 |
| --- | --- |
| Max. at 300 nm. | |

Analysis: m.w. 432.62):

| | C % | H % | S % |
| --- | --- | --- | --- |
| Calculated | 77.73 | 7.45 | 7.41 |
| Found | 77.8 | 7.6 | 7.1 |

EXAMPLE 4
(17R) 4',5'-dihydro-11-beta-[4-(methylthio)phenyl]-spiro(estra-4,9-dien-17,2'-(3H)-furan)-3-one

Stage A: (1,2-ethanediyl) cyclic acetal of 5-alpha,17-beta-dihydroxy-11-beta-[4-(methylthio)-phenyl]-17-alpha-[3-(tetrahydro-2H-2-pyrannyloxy)-propyl]estr-9-en-3-one 2.1 g of 3,3-(1,2-ethanediyl) cyclic acetal of 5-alpha,17-beta-dihydroxy-11-beta-[4-(methylthio)-phenyl]-17-alpha-[3-(tetrahydro-2H-2-pyrannyloxy)-1-propynyl]-9-en-3-one is dissolved in 21 cm³ of benzene and 21 cm³ of ethanol, 840 mg of Wilkinson's reagent [chlorotris (triphenylphosphine) rhodium]is added, and the whole is submitted to hydrogenation for 16 hours. 420 mg of Wilkinson's reagent is added, and hydrogenation is continued for a further 3 hours. After concentrating to dryness by distilling under reduced pressure, chromatographing the residue on silica, eluting with a mixture of cyclohexane and ethyl acetate (6/4), there is obtained:

336 mg of ethylene compound, identical to the product obtained at stage C of example 3, 185 mg of a mixture of ethylene compound of the initial product and of the compound sought, 1.042 g of the compound sought, used as it is for the following stage.

IR Spectrum (chloroform): —OH at 3600 cm$^{-1}$; 3504 cm$^{-1}$, aromatics at 1600 cm$^{-1}$, 1492 cm$^{-1}$.

NMR Spectrum (deuterochloroform): Peak at 0.50 ppm, hydrogens of the methyl at 18; Peak at 2.46 ppm, hydrogens of the methyl of —SCH$_3$; Peaks from 3.33 to 4.55 ppm, hydrogens in position 11 and hydrogens of CH$_2$O; Peak at 4.63 ppm, hydrogen of ketal of the THP Peak at 7.17 ppm, aromatic hydrogens.

Stage B:
17-beta-hydroxy-17-alpha-(3-hydroxypropyl)-11-beta-[4-(methylthio)phenyl]estra-4,9-dien-3-one 1.51 g of 3,3-(1,2-ethanediyl) cyclic acetal of 5-alpha,17-beta-dihydroxy-11-beta-[4-(methylthio)-phenyl]-17-alpha-[3-(tetrahydro-2H-2-pyrannyloxy)-propyl]estra-9-en-3-one. obtained at stage A is dissolved in 25 cm$^3$ of methanol, 11.5 cm$^3$ of an aqueous solution of hydrochloric acid diluted to ½ is added, with agitation under inert atmosphere at 20° C. for 30 minutes; after dilution with water, extraction is done with methylene chloride. The extracts are dried, concentrated to dryness by distilling under reduced pressure, then the residue obtained is chromatographed on silica, eluting with a mixture of ether and ethyl acetate (1/1), so obtaining:

768 mg of the product sought.

IR Spectrum (chloroform): free OH at 3620 cm$^{-1}$+combined at 3410 cm$^{-1}$; dienone at 1653 cm$^{-1}$ and 1601 cm$^{-1}$; aromatics at 1555 cm$^{-1}$ and 1492 cm$^{-1}$.

Stage C: (17R)
4′,5′-dihydro-11-beta-[4-(methylthio)phenyl]-spiro(estra-4,9-dien-17,2′-(3H)-furan)-3-one 1.04 g of 17-beta-hydroxy-17-alpha-(3-hydroxypropyl)-11-beta-[4-(methylthio)phenyl]estra-4,9-dien-3-one obtained at stage B is dissolved in 20 cm$^3$ of pyridine, 2.1 g of tosyl chloride is added, with agitation for 1 hour at 20° C. After diluting with water and ice, extraction is done with ethyl acetate. The extracts are washed with a dilute aqueous solution of hydrochloric acid, then with water and with an aqueous solution of sodium bicarbonate, dried, and concentrated to dryness by distilling under reduced pressure. The residue obtained is crystallized from a mixture of methylene chloride and ethanol, so obtaining 818 mg of the product sought, m.p. 105° C. (not very clear).

IR Spectrum (chloroform): —C —O—C— at 1076 cm$^{-1}$, 1055 cm$^{-1}$; dienone at 1653 cm$^{-1}$, 1602 cm$^{-1}$; aromatics at 1555 cm$^{-1}$, 1493 cm$^{-1}$.

NMR Spectrum (deuterochloroform); Peak at 0.57 ppm, hydrogens of the methyl at 18; Peak at 2.46 ppm, hydrogens of the methyl of —SCH$_3$; Peaks at 3.78 ppm, hydrogens of CH$_2$—O—; Peaks from 4.35 to 4.42 ppm, hydrogens in position 11; Peak at 5.81 ppm, hydrogen at position 4; Peak at 7.17 ppm, aromatic hydrogens.

Analysis: C$_{28}$H$_{34}$O$_2$S (434.64):

|  | C % | H % |
|---|---|---|
| Calculated | 77.37 | 7.88 |
| Found | 77.1 | 8.0 |

EXAMPLE 5
(17R) 11-beta-(2-methoxyphenyl)-spiro(estra-4,9-dien-17,2′-(5H)-furan-3-one Stage A: (Z) 3,3-dimethoxyketal of 5-alpha,10-alpha-epoxy-17-beta-hydroxy-17-alpha-[3-tetrahydro-(2H)-2-pyrannyloxy)-1-propynyl]estra-9(11)-en-3-one 400 cm$_3$ of a 1.6M solution of butyllithium in hexane is cooled to 0° C., and at this temperature, 98 g of the reagent HC≡C—CH$_2$OTHP in 180 cm$^3$ of tetrahydrofuran is added, with agitation for 30 minutes at 0° C.

66.4 g of dimethoxy ketal of 5-alpha,10-alpha-epoxy-estra-9(11)-en-3,17-dione in solution in 200 cm$^3$ of tetrahydrofuran is added drop by drop, with agitation for 2 hours. while allowing the temperature to return to the ambient. The reactional mixture is then poured into an aqueous solution of ammonium chloride and extracted with ethyl acetate and then with methylene chloride. The organic phases are put together, washed with water, dried, and then the solvents are eliminated under reduced pressure. The residue is chromatographed on silica, (eluent—cyclohexane—ethyl acetate, 7-3 with 1% of triethylamine). 53 g of crude product is obtained which is purified by chromatography on silica (eluent, methylene chloride—acetone 95/5, with 1% of triethylamine).

Stage B: (Z) 3,3-dimethoxy ketal of 5-alpha,10-alpha-epoxy-17-beta-hydroxy-17-alpha-[3-(tetrahydro-(2H)-2-pyrannyloxy)-1-propenyl]estra-9(11)-en-3-one 2.5 g of the crude product obtained at stage A in 400 cm$^3$ of ethyl acetate is hydrogenated for 30 minutes under a pressure of 1100 mb, in the presence of 25 mg of palladium at 10% on barium sulphate and 1 cm$^3$ of pyridine. After filtering off the catalyst, washing and extracting with ethyl acetate, the organic phases are put together and the solvents are eliminated under reduced pressure. 2.5 g of crude product is recovered, which is purified by chromatography on silica (eluent, methylene chloride—acetone, 95-5).

728 mg of the expected product is obtained.

IR Spectrum, (CHCl$_3$): OH 3,600 cm$^{-1}$, 3,400 cm$^{-1}$ (F).

Presence of epoxy.

Stage C: (Z) 3,3-dimethoxy ketal of 5-alpha,17-beta-dihydroxy-11-beta-(2-methoxyphenyl)-17-alpha-[3-(tetrahydro-(2H)-2-pyrannyloxy)-1-propenyl]estr-9-en-3-one Prepration of the magnesium compound The operation is one as at stage B of example 3, starting with magnesium and orthobromo anisole. A solution is obtained titrating 0.72M/l.

Condensation 3 g of the product obtained at the preceding stage is dissolved in 60 cm$^3$ of tetrahydrofuran under an inert atmosphere, then 187 mg of cuprous chloride is added, with heating to 34° C.±1° C. Over 20 minutes, 26.2 cm³ of the magnesium compound prepared above is introduced, with agitation for 16 hours. The temperature is allowed to return to the ambient, then the reactional mixture is poured into a solution of ammonium chloride, agitated for 15 minutes, then extraction is done with ethyl acetate. The extracts are washed with an aqueous solution of sodium chloride, dried and concentrated to dryness under reduced pressure. 6.58 g crude product is obtained, which is purified by chromatography on silica (eluent, methylene chloride-acetone 92-8, with 1% of triethylamine).

IR Spectrum (CHCL₃): OH, free 3,600 cm⁻¹, combined 3,450 cm⁻¹; aromatics, 1,597 cm⁻¹, 1,584 cm⁻¹, 1,490 cm⁻¹.

Stage D. (Z) 11-beta-(2-methoxyphenyl-17-beta-hydroxy-17-alpha-(3-hydroxy-1-propenyl)estra-4,9-dien-3-one At ambient temperature, 1.08 g of the product obtained at stage B is dissolved in 10 cm³ of ethanol, and a solution of 1.08 g of potassium hydrogensulphate in 6.5 cm³ of water is added and agitated for 5 hours at ambient temperature. After eliminating the ethanol, extraction is done with methylene chloride, the organic phase is washed with water, dried and concentrated to dryness under reduced pressure. After chromatography on silica (eluent, cyclohexane-ethyl acetate, 1-1) 0.703 g of the expected product is obtained.

IR Spectrum (CHCl₃): OH, free 3,612 cm⁻¹ and combined 3,415 cm⁻¹ dienone, 1,654 cm⁻¹ 1,597 cm⁻¹ aromatic, 1,488 cm⁻¹.

Stage E; (17R) 11-beta-(2-methoxyphenyl)-spiro(spiro(estra-4,9-dien-17,2'-(5H)-furan-3-one At ambient temperature, 0.661 g of the product obtained in the preceding stage is dissolved in 13.2 cm³ of pyridine, the solution is cooled to 0° C., and over 5 minutes, 1.32 g of tosyl chloride is added, then the temperature is allowed to return to the ambient, and agitation is maintained for 1 hour. The temperature is again lowered to 0° C., and 14 cm³ of 6N hydrochloric acid is added. After decanting, the aqueous phase is extracted with ethyl acetate, washed with water, dried, and the solvents are eliminated under reduced pressure. After chromatography on silica, (eluent: cyclohexane - ethyl acetate, 8-2), 0.459 g of the expected product is obtained.

IR Spectrum (CHCl₃): dienone 1,655 cm⁻¹, 1,597 cm⁻¹, aromatic 1,488 cm⁻¹.

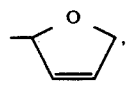

1,080 cm⁻¹, 1,040 cm⁻¹.

EXAMPLE 6 (17R)-11-beta-(4-chlorophenyl)-4',5'-dihydro-spiro(estra-4,9-dien-17,2'-(3H)-furan-3-one

Stage A: Dimethyl ketal of 5-alpha,10-alpha-epoxy-17-beta-hydroxy-17-alpha-[3-tetrahydro-2H-2-pyrannyloxy)propyl]-estr-9(11)-en-3-one 6 g of 3,3-dimethoxy ketal of 5-alpha,10-alpha-epoxy-17-beta-hydroxy-17-alpha-[3-(tetrahydro-2H-2-pyranyloxy)-1-propynyl]estra-9(11)-ene-3-one, prepared as at stage A of Example 5 is dissolved in 60 cm³ of benzene, and submitted to a hydrogenation under 1,860 mbars in the presence of 1.5 g of Wilkinson's reagent for 7 hours. The mixture is then diluted with ether, filtered, and the filtrate is concentrated to dryness under reduced pressure, and 7.7 g of crude product is collected which is chromatographed on silica (eluent: petroleum ether (b.p. 40°-70° C.) and ethyl acetate 4–6). 4.95 g of the expected proeuct is obtained.

IR-Spectrum (CHCl₃): OH, free, 3,620 cm⁻¹, 3,600 cm⁻¹, —C≡C—, 1,640 cm⁻¹.

Stage B: Dimethyl ketal of 11-beta-(4-chlorophenyl)-5-alpha,17-betadihydroxy-17-alpha-[3-(tetrahydro-2H-2-pyrannyloxy)propyl]-estr-9(11)-en-3-one Preparation of the magnesium compound:
The operation is done as at stage B of Example 3, starting with 1.22 g of magnesium and 3 cm³ of the solution prepared, starting with 7.65 g of parabromochlorobenzene in 50 cm³ of tetrahydrofuran. A magnesium compound titrating 0.65M/l is obtained.

Condensation

The operation is done as at stage B of Example 3, using 23 cm³ of the magnesium compound solution, 165 mg of cuprous chloride and 2.46 g of the product obtained in the preceding stage A in solution in 12 cm³ of tetrahydrofuran. After chromatography on silica, (eluent: petroleum ether (b.p. 40°-70° C.) and ethyl acetate, 1—1), 2 g is recovered of the crude product expected, which is used as it is for the following stage.

IR Spectrum (CHCl₃): OH at 5 3,478 cm⁻¹, OH at 17 max. 3,620 cm⁻¹. shoulder, 3,600 cm⁻¹, aromatic bands

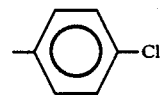

1,599 cm⁻¹, 1,489 cm⁻¹, —OCH₃, 2,835 cm⁻¹.

Stage C: 11-beta-(4-chlorophenyl)-17-beta-hydroxy-17-alpha-(3-hydroxypropyl)-estra-4,9-dien-3-one 15 cm³ of 2N hydrochloric acid is added to 1.99 g of the product obtained in the preceding stage, in 20 cm³ of methanol.

The mixture is heated to 50° C. for 45 minutes, then poured into an aqueous solution of sodium bicarbonate and extracted with ethyl acetate. The organic phases are dried and conecentrated to dryness under reduced pressure. 1.42 g of the expected product is obtained, with m.p. 262° C. after recrystallizing from a mixture of methylene chloride and isopropyl ether.

IR-Spectrum (CHCl3): OH fre combined, 3,620 cm$^{-1}$, dienone 1,655 cm$^{-1}$, 1,602 cm$^{-1}$.

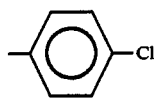

aromatic bands, 1-570 cm$^{-1}$, 1,490 cm$^{-1}$.
Analysis: C$_{27}$H$_{31}$ClO$_2$ (422.99):

|  | C % | H % | Cl % |
|---|---|---|---|
| Calculated | 73.53 | 7.54 | 8.03 |
| Found | 73.3 | 7.8 | 8.3 |

Stage D: (17R) 11-beta-(4-chlorophenyl-4'.5'-dihydro-spiro(estra-4,9-dien-17,2'-(3H)-furan-3-one Under an inert atmosphere, 1 g of the product obtained at stage C is dissolved in 20 cm$^3$ of pyridine, then cooled to 0° to +5° C. and 2.2 g of tosyl chloride is added, with agitation for 1 hour and 30 minutes at ambient temperature. The reactional mixture is poured into iced water, agitated for 15 minutes, then extracted with ethyl acetate, and washed with a saturated aqueous solution of sodium bicarbonate. The precipitate formed is separated, dried and 694 mg of the expected product is obtained.

The filtrate is dried, the solvent is eliminated under reduced pressure, the residue is chromatographed on silica (eluent: cyclohexane-ethyl acetate, 6-4) and the expected product is obtained, which is recrystallized from a mixture of ethanol and chloroform (2-1). m.p. 308° C.

IR Spectrum (CHCl3): dienone 1,654 cm$^{-1}$, 1,603 cm$^{-1}$,

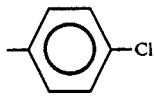

aromatics, 1,572 cm$^{-1}$, 1,490 cm$^{-1}$.

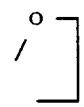

1,078 cm$^{-1}$, 1,055 cm$^{-1}$.
Analysis: C$_{27}$H$_{31}$ClO$_2$ (422.99):

|  | C % | H % | Cl % |
|---|---|---|---|
| Calculated | 76.66 | 7.38 | 8.38 |
| Found | 76.7 | 7.4 | 9 |

EXAMPLE 7

(17R) 4'5'-dihydro-11-beta-(4-methoxyphenyl)-spiro(estr-4,9-diene-17,2'-(3H)-furan)-3-one

Stage A: dimethylketal of 5-alpha,17-beta-dihydroxy-11-beta-(4-methoxyphenyl)-17-alpha-[3-(tetrahydro-2H-2-pyrannyloxy)propyl]-estr-9-en-3-one Preparation of the magnesium compound The operation is done as in stage B of Example 3, starting with 1.45 g of magnesium and 9.15 g of para-bromoanisole in 45 cm$^3$ of tetrahydrofuran. A magnesium compound titrating 0.9M/l is obtained.

Condensation

The operation is done as in Example 3, using 15 cm$^3$ of magnesium compound prepared as above, 15 cm$^3$ of tetrafuran, 165 mg of cuprous chloride and 2.4 g of the product prepared at stage A of Example 6. After chromatography on silica (eluent, petroleum ether (b.p. 40°-70° C.), and ethyl acetate, 1—1), 6 g of the expected product is collected, used as it is in the following stage.

Stage B: 17-beta-hydroxy-17-alpha-(3-hydroxypropyl)-11-beta-(4-methoxyphenyl)-estra-4,9-dien-3-one The operation is done as in stage C of Example 6, starting with 6 g of the product obtained at stage A. 5 g of the crude product expected is obtained, which is purified by chromatography on silica, eluting with a mixture of methylene chloride and acetone, 7-3.

IR Spectrum (CHCl3):

| OH free + combined, | 3,620 cm$^{-1}$ |
| C = 0 | 1,656 cm$^{-1}$, |
| C = C | 1,608 cm$^{-1}$, 1,509 cm$^{-1}$. |
| aromatic | |

Stage C: (17R) 4'5'-dihydro-11-beta-(4-methoxyphenyl)-spiro-(estr-4,9-diene-17,2'-(3H)-furan)-3-one The operation is done as at stage D of Example 6, starting with 655 mg of product obtained at stage B and 1.4 g of tosyl chloride. After chromatography, 650 mg of crude product is obtained, which is recrystallized from a mixture of methylene chyloride and isopropyl ether. 500 mg of the expected product is collected. m.p. 192° C.

IR Spectrum (CHCl3):

| C = 0 | 1,655 cm$^{-1}$, | |
| C = C aromatic | 1,608 cm$^{-1}$,(max) 1,509 cm$^{-1}$, | 1,582 cm$^{-1}$ (shoulder) |
| C—O—C | 1,078 cm$^{-1}$, | 1,055 cm$^{-1}$ |

Analysis: C$_{28}$H$_{34}$O$_3$ (418.58):

|  | C % | H % |
|---|---|---|
| Calculated | 80.34 | 8.18 |

|   | C % | H % |
|---|---|---|
| Found | 80.2 | 8.2 |

[alpha]$_D$ = +133.5°±2.5° (C=1% CHCl$_3$).

EXAMPLE 8

(17R) 11-beta-(3-thienyl)-spiro(estra-4,9-dien-17,2'-(5H)-furan)-3-one

Stage A: (Z) (1,2-ethanediyl) cyclic acetal of 5-alpha,10-alphaepoxy-17-alpha-[3-(tetrahydro-2H-2-pyrannyloxy)-1-propenyl]-estr-9(11)-en-3-one 940 mg of the product prepared at stage A of Example 3 is dissolved in 20 cm$^3$ of ethyl acetate in the presence of 5 cm$^3$ of pyridine. 9 mg of palladium at 10% on barium sulphate is added, and the mixture is hydrogenated for 24 minutes at atmospheric pressure. The catalyst is filtered off, the filtrate is rinsed with ethyl acetate and concentrated to dryness. 965 mg of crude product is obtained which is chromatographed on silica (eluent; methylene chloride - ethyl acetate, 8-2).

795 mg of the expected product is recuperated.

IR Spectrum (CHCl$_3$): OH free 3,600 cm$^{-1}$, combined, about 3,400 cm$^{-1}$, delta 9-11 1,640 cm$^{-1}$, epoxy 971 cm$^{-1}$.

Stage B: (Z) (1,2-ethanediyl) cyclic acetal of 5-alpha-17-beta-dihydroxy-17-alpha-[3-(tetrahydro-2H-2-pyrannyl-oxy)-1-propenyl]-11-beta-(3-thienyl)-estr-9-en-3-one Preparation of the magnesium compound The operation is done as in Example 3 (stage B), starting with magnesium and with 3-bromothiophene. A solution is obtained, titrating 0.6M/l.

Condensation

A suspension comprising 35.2 cm$^3$ of the magnesium compound prepared above in 14 cm$^3$ of tetrahydrofuran is cooled to −20° C., 0.210 g of cuprous choride is added, with agitation for 10 minutes. A solution of 2.5 g of the product obtained at stage A in 25 cm$^3$ of tetrahydrofuran is added, drop by drop, while maintaining the temperature at −20° C., and agitating for 1 hour. After allowing the temperature to return to the ambient, 10 cm$^3$ of ammonium chloride in saturated solution is added drop by drop, then the reactional medium is poured into 90 cm$^3$ of a saturated solution of ammonium chloride and agitated for 15 minutes. After decanting, the aqueous phase is extracted with ethyl acetate. The organic phase is washed with water, dried, and the solvents are eliminated under reduced pressure.

4.68 g of crude product is obtained which is chromatographed on silica (eluent: cyclohexane - ethyl acetate, 6-4, with 1% of triethylamine. 2.107 g of the expected product is obtained, m.p. 158° C.

IR Spectrum (CHCl$_3$): OH at position 5, 3,501 cm$^{-1}$.

Stage C: (Z) 17-beta-hydroxy-17-alpha-(3-hydroxy-1-propenyl)-11-beta-(3-thienyl)-estra-4,9-dien-3-one Under an inert atmosphere, 2.1 g of the product obtained in the preceding stage is dissolved in 42 cm$^3$ of ethanol, 6.3 cm$^3$ of a 2N aqueous solution of hydrochloric acid is added, with agitation for 3 hours at ambient temperature. After cooling to about 5° C., 42 cm$^3$ of water is added progressively, with agitation for 30 minutes. The precipitate is separated, washed with water until neutral, then dissolved in methylene chloride and dried. The solvents are eliminated under reduced pressure, and 1.15 g of the expected product is obtained. m.p. 240° C.

IR Spectrum (CHCl$_3$): OH free and combined, 3,611 cm$^{-1}$, dienone 1,657 cm$^{-1}$ 1,603 cm$^{-1}$.

Stage D: (17R) 11-beta-(3-thienyl)-spiro(estra-4,9-dien-17,2'-(5H)-furan-3-one The operation is done as at stage D of Example 5, utilizing 1.15 g of the product prepared in the preceding stage, 23 cm$^3$ of pyridine, 2.3 g of tosyl chloride and 23 cm$^3$ of 6N hydrochloric acid.

1.03 g of crude product is obtained which is purified by chromatography on silica, eluting with methylene chloride and acetone, (98-2). 0.755 g of the expected product is collected, which is recrystallized from isopropanol. m.p. 242° C.

IR Spectrum (CHCl$_3$): dienone 1,654 cm$^{-1}$, 1,603 cm$^{-1}$,

1,520 cm$^{-1}$,

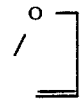

1,080 cm$^{-1}$.

Analysis: C$_{25}$H$_{28}$O$_2$S: 392.565:

|   | C % | H % | S % |
|---|---|---|---|
| Calculated | 76.49 | 7.18 | 8.16 |
| Found | 76.4 | 7.3 | 8.0 |

EXAMPLE 9

(17R) 11-beta-(4-acetylphenyl)-spiro(estra-4,9-dien-17,2'-(5H)-furan)-3-one

Stage A: (Z) (1,2-ethanediyl) cyclic acetal of 5-alpha,17-beta-dihydroxy-11-beta-[4-(2-methyl-1,3-dioxolan-2-yl)phenyl]-17-alpha-[3-tetrahydro-2H-2-pyrannyloxy)propenyl]estr-9-en-3-one Preparation of the magnesium compound The operation is done as at stage B of example 3, starting with 1.45 g of magnesium and 12.15 g of ethylene ketal of parabromoacetophenone. A suspension is obtained, titrating 0.8M.

Condensation

Under an inert atmosphere, 21 mg of cuprous chloride is added to 8 cm$^3$ of the magnesium compound suspension, cooled to 0° to +5° C., and agitated for 15 minutes. Then 1 g of the product prepared at stage A of example 8 in solution in 15 cm$^3$ of tetrahydrofuran is added drop by drop, and agitated for 1 hour at ambient temperature. The reactional medium is poured into an aqueous solution of ammonium chloride and extracted with ethyl acetate. The organic phase is washed with water, dried and concentrated to dryness. 3.5 g of crude product is obtained, which is purified by chromatography on silica, (eluent: cyclohexane-ethyl aacetate 1-1).

IR Spectrum (CHCl₃:

| | |
|---|---|
| OH at 5 | 3500 cm⁻¹, |
| OH + combined | 3600 cm⁻¹ |
| aromatics | 1605 cm⁻¹ |
| C = C | 1502 cm⁻¹. |

Stage B: (Z) 11-beta-(4-acetylphenyl)-17-beta-hydroxy-17-alpha-(3-hydroxy-1-propenyl)-estra-4,9-dien-3-one 2.07 g of the product prepared in the preceding stage is dissolved in 40 cm³ 1 of methanol, 16 cm³ of a 2N aqueous solution of hydrochloric acid is added, with agitation for 1 hour 30 minutes at 50° C. The reactional medium is poured into an aqueous solution of sodium bicarbonate, extracted with ethyl acetate, washed with water, dried, and concentrated to dryness under reduced pressure. 1.63 g of crude product is obtained which is chromatographed on silica (eluent: methylene chloride - acetone, 7-3), then recrystallized from ethanol. 1.48 g of the expected product is collected, m.p. about 130° C.

IR Spectrum (CHCl₃):

| | |
|---|---|
| C = 0 | 1678 cm⁻¹ |
| —CH₃ | 1359 cm⁻¹ |
| C = C + aromatic | 1604 cm⁻¹, 1565 cm⁻¹ |
| dienone | 1657 cm⁻¹ |
| OH free | 3609 cm⁻¹ |
| OH combined | 3410 cm⁻¹. |

Analysis: C₂₉H₃₄O₄: 444.57:

| | C % | H % |
|---|---|---|
| Calculated | 77.99 | 7.67 |
| Found | 78 | 7.7 |

Stage C: (17R)-11-beta-(4-acetylphenyl)-spiro(estra-4,9-dien-17,2′-(5H)-furan)-3-one Under an inert atmosphere, 0.704 g of product prepared in the preceding stage is dissolved in 16 cm³ of pyridine, then cooled to 0° C. 1.49 g of tosyl chloride is added, with agitation for 2 hours and allowing the temperature to return to the ambient. The reactional medium is poured into iced water, agitated for 15 minutes, extracted with ethyl acetate, washed with a solution of sodium bicarbonate, dried and evaporated to dryness. 0.775 g of crude product is obtained which is chromatographed on silica (eluent: cyclohexane-ethyl acetate 1-1), then recrystallized from a mixture of ethanol and methylene chloride. 0.555 g of the expected product is collected. m.p. about 125°-130° C.

IR Spectrum (CHCl₃):

| | |
|---|---|
| C = 0 | 1678 cm⁻¹ |
| CH₃ | 1359 cm⁻¹ |
| C = C + aromatic | 1604 cm⁻¹, 1565 cm⁻¹ |
| dienone | 1657 cm⁻¹ |

[alpha]$_D$ = +231.5°±3° (c=1% CHCl₃).
Analysis: C₂₉H₃₂O₃: 428.57:

| | C % | H % |
|---|---|---|
| Calculated | 81.27 | 7.52 |
| Found | 81.1 | 7.8 |

EXAMPLE 10

(17 R) 11-beta-[4-(methylthio)phenyl]-spiro(estra-5(10),9(11)-dien-17,2′-(5′H)-furan)-3-one and (17 R) 11-beta-[4-methylthio)phenyl]-spiro(estra-4,9-dien-17,2′-(5H)-furan)-3-one 1.5 g of the product prepared at stage C of example 3 is dissolved in 30 cm³ of methanol and 15 cm³ of 1N hydrochloric acid is added. A further 30 cm³ of methanol and 30 cm³ of dioxan are added, with agitation for 2 hours at ambient temperature. The reactional medium is poured into water, extracted with methylene chloride, concentrated to dryness, and 1.23 g of residue is obtained, which is dissolved again in 25 cm³ of pyridine. 1.91 g of tosyl chloride is added, with agitation for 1 hour 30 minutes at ambient temperature, followed by pouring into iced water and extracting with ethyl acetate. The organic phase is washed with an aqueous solution of hydrochloric acid, then with an aqueous solution of sodium chloride, washed and concentrated to dryness. 1.12 g of crude product is collected, which is chromatographed on silica (eluent: methylene chloride - ethyl acetate, 9-1), and 98 mg of the expected product is obtained, and 863 mg of the corresponding 4,9-diene. (identical to the product obtained at example 3, stage E).

IR Spectrum (CHCl₃) of the estra-5(10),9(11)-diene. C=O: 1712 cm⁻¹, C=C+aromatic: 1590 cm⁻¹, C=C of the spirocycle: 1626 cm⁻¹.

IR Spectrum (CHCl₃) of the estra-4,9-diene C=O: 1653 cm⁻¹, C=C conjugated with C=O: 1600 cm⁻¹, aromatic: 1492 cm⁻¹.

EXAMPLE 11

N-oxide of (17R) 4′,5′-dihydro-11-beta-[4-(dimethylamino)phenyl]-spiro(estra-4,9-dien-17,2′-(3H)-furan)-3-one Under reduced pressure, 1.43 g of (17R) 4′,5′-dihydro-11-beta-[4-(dimethylamino)phenyl]-spiro(estra-4,9-dien-17,2′-(3H)-furan)-3-one prepared at example 1, (product B) is dissolved in 30 cm³ of methylene chloride, and cooled to 0° to +5° C. Over 15 minutes, 0.666 g of metachloroperbenzoic acid in solution at 85% in methylene chloride is added.

After one-and-a-half hours of agitation at 0° to +5° C. the reactional medium is poured into 100 cm³ of a 0.2N solution of sodium thiosulphate and is extracted with methylene chloride. After washing with an aqueous solution of sodium bicarbonate, then with water, drying and eliminating the solvents, 11.8 g of crude product is collected which is chromatographed on silica (eluent: methylene chloride - methanol, 7-3). 1.34 g is obtained of the expected product (solvate containing methylene chloride), which is lyophilised.

IR Spectrum (CHCl$_3$): —C=O: 1,655 cm$^{-1}$ C=C and aromatic: 1,602 cm$^{-1}$, 1,498 cm$^{-1}$.
[alpha]$_D$+128°±2° (c=1% ethanol).

EXAMPLE 12

(17R)
4'5'-dihydro-11-beta-[4-(1-methylethyl)phenyl]spiro(estra-4,9-dien-17,2'-(3H)-furan)-3-one

Stage A: (1,2-ethanediyl) cyclic acetal of 5-alpha,10-alpha-epoxy-17-beta-hydroxy-17-alpha-[3-(tetrahydro-2H-2-pyrannyloxy)propyl]-estr-9(11)-en-3-one The operation is done as in example 6, stage A, using 1 g of the product (1,2-ethanediyl) cyclic acetal of 17-beta-hydroxy-5-alpha, 10-alpha-epoxy-17-alpha-[3-(tetrahydro-2H-2-pyrannyloxy-1-propynyl]-estr-9(11)-en-3-one prepared at example 3 stage A and 0.25 g of Wilkinson's catalyst. 1.28 g of the expected product is obtained.

IR Spectrum (CHCl$_3$): OH free 3,620 cm$^{-1}$, 3,605 cm$^{-1}$, OH combined, strong 3,485 cm$^{-1}$, C=C 1,643 cm$^{-1}$.

Stage B: (1,2-ethanediyl) cyclic acetal of 5-alpha,17-beta-dihydroxy-11-beta-[4-(1-methylethyl)-phenyl-17-alpha-[3-(tetrahydro-2H-2-pyrannyloxy)-propyl]-estr-9-en-3-one 2.45 g of product prepared as at stage A in solution in 10 cm$^3$ of tetrahydrofuran is cooled to 0° C., 110 mg of cuprous chloride is added, with agitation for 10 minutes, then, over 15 minutes, 32 cm$^3$ of 4-isopropylphenyl magnesium bromide in solution at 0.66 M/l in tetrahydrofuran is added. After agitating this for 2 hours at +3° C.±1° C. it is poured into an iced aqueous solution of ammonium chloride, and extracted with ether and then with methylene chloride. The extracts are dried and the solvents are eliminated under reduced pressure. 4.65 g of crude product is obtained which is chromatographed on silica, (eluent: cyclohexane-ethyl acetate), and is used as it is for the following stage.

Stage C: 17-beta-hydroxy-17-alpha-(3-hydroxypropyl)-11-beta-[4-(1-methylethyl)phenyl]-estra-4,9-dien-3-one 2.58 g of the product obtained in the preceding stage is agitated for 2 hours at ambient temperature in 20 cm$^3$ of ethanol with 5 cm$^3$ of 2N hydrochloric acid. After concentrating to a small volume under reduced pressure, extracting with methylene chloride, washing, drying and eliminating the solvent under reduced pressure, 2.2 g of the expected product is obtained. This is purified by chromatography on silica (eluent: n-hexane-ethyl acetate, 3-7).

IR Spectrum (CHCl$_3$): OH free 3,620 cm$^{-1}$+combined. dienone 1,655 cm$^{-1}$ to 1,601 cm$^{-1}$. aromatic 1,590 cm$^{-1}$.

Stage D: (17R) 4'5'-dihydro-11-beta-[4-(1-methylethyl)phenyl]-spiro(estra-4,9-dien-17,2'-(3H)-furan)-3-one 1.15 g of the product obtained previously, 20 cm$^3$ of pyridine and 2.1 g of tosyl chloride are agitated for one and a half hours at ambient temperature. After diluting with 50 cm$^3$ of water and ice, 20 cm$^3$ of concentrated hydrochloric acid is added slowly, then the aqueous phase is extracted with methylene chloride, dried, and the solvents are eliminated under reduced pressure. 1.686 g of crude product is obtained, which is chromatographed on silica (eluent: methylene chloride - acetone, 95-5), then recrystallized from ethanol. 659 mg of the expected product is collected. m.p. 114° C.

IR Spectrum (CHCl$_3$):

| Ketone, conjugated: 1,654 cm$^{-1}$ | | |
|---|---|---|
| C=C aromatic | 1,601 cm$^{-1}$ | 1,510 cm$^{-1}$ |

Analysis: C$_{30}$H$_{38}$O$_2$: 430.635:

|  | C % | H % | S % |
|---|---|---|---|
| Calculated | 83.68 | 8.89 | |
| Found | 83.8 | 9.1 | |

EXAMPLE 13

(17R)
11-beta-[3-(methylthio)phenyl)-spiro(estra-4,9-dien-17,2'-(5H)-furan)-3-one

Stage A: (1,2-ethanediyl) cyclic acetal of 5-alpha-17-beta-dihydroxy-11-beta-[3-(methylthio)-phenyl]-17-alpha-[3-(1-tetrahydro-2H-2-pyrannyloxy)-1-propenyl]-estr-9-en-3-one The operation is done as at stage B of example 8, using 2.5 g of the product prepared at stage A of example 8, 110 mg of cuprous chloride and 18 cm$^3$ of the magnesium compound prepared as in example 3, starting with 3-bromothioanisole and titrating 1.17 M/l. 3 g of the expected product is obtained.

IR Spectrum (CHCl$_3$): OH free about 3,600 cm$^{-1}$+combined 3,498 cm$^{-1}$ (max.) 3,440 cm$^{-1}$ (shoulder). aromatic 1,587 cm$^{-1}$ 1,568 cm$^{-1}$.

Stage B: (Z)-17-beta-hydroxy-17-alpha-(3-hydroxy-1-propenyl)-1 1-beta-[2-(methylthio)phenyl]-estra-4,9-dien-3-one At ambient temperature, 3 g of the product obtained previously, 30 cm$^3$ of ethanol and 5 cm$^3$ of 2N hydrochloric acid are mixed together for 2 hours, then concentrated to a small volume under reduced pressure, extracted with methylene chloride, washed and dried, and the solvents are eliminated under reduced pressure. The residue is chromatographed on silica (eluent: cyclohexane-ethyl acetate 5-5), and 1.083 g of the expected product is collected. m.p. 168° C.

IR Spectrum: (CHCl$_3$): OH 3,613 cm$^{-1}$+combined 3,440 cm$^{-1}$, dienone 1,656 cm$^{-1}$ to 1,601 cm$^{-1}$, aromatic 1,587 cm$^{-1}$ 1,569 cm$^{-1}$ 1,474 cm$^{-1}$.

Stage C: (17R)-11-beta-[3-(methylthio)phenyl)-spiro(estra-4,9-dien-17,2'-(5H)-furan)-3-one The operation is done as at stage D of example 12, starting with. 1.050 g of product obtained in the previous stage B, and 592 mg of the pure expected product is obtained.

IR Spectrum (CHCl$_3$): dienone 1,657 cm$^{-1}$ to 1,601 cm$^{-1}$, aromatic, 1,587 cm$^{-1}$ 1,569 cm$^{31\ 1}$ 1,473 cm$^{-1}$, —C—O—C—, 1,080 cm$^{-1}$ to 1,041 cm$^{-1}$.

Analysis: C$_{28}$H$_{32}$O$_2$ 432.62:

|  | C % | H % | S % |
|---|---|---|---|
| Calculated | 77.7 | 7.46 | 7.41 |
| Found | 77.6 | 7.4 | 7.1 |

EXAMPLE 14 (17R)
11-beta-(4-chlorophenyl)-spiro(estra-4,9-dien-17,2'-(5H)-furan)-3-one Stage A: (Z) (1,2-ethanediyl) cyclic acetal of 11-beta-(4-chlorophenyl)-5-alpha,17-beta-dihydroxy-17-alpha-[3-tetrahydro-2H-2-pyrannyloxy)-1-propenyl]-estr-9-en-3-one The operation is done as at stage B of example 8, starting with 2,5 g of the product prepared at stage A of example 8, 160 mg of cuprous chloride and 18 cm³ of a magnesium compound solution prepared as in example 3, starting with 4-chlorobromobenzene, and titrating 0.87M/l. 3.082 g of the pure expected product is obtained.

IR Spectrum: OH, 3,500 cm$^{-1}$+combined, towards 3,405 cm$^{-1}$, aromatic, 1,600 cm$^{-1}$ 1,490 cm$^{-1}$.

Stage B: (Z) 11-beta-(4-chlorophenyl)-17-beta-hydroxy-17-alpha-(3-hydroxy-1-propenyl)-estr-4,9-dien-3-one At ambient temperature, 3.05 g of the product obtained in the preceding stage is agitated for 3 hours in 30 cm³ of ethanol and 30 cm³ of water, in the presence of 3 g of potassium hydrogenosulphate.

The mixture is concentrated to a small volume under reduced pressure, then diluted with water and extracted with methylene chloride; the extracts are dried and the solvents are eliminated under reduced pressure. 2.54 g of crude product is obtained, which is chromatographed on silica (eluent, cyclohexane and ethyl acetate, 5-5), then crystallized from ethyl acetate. m.p. 214° C.

IR Spectrum (CHCl$_3$): OH about 3,611 cm$^{-1}$+combined, dienone 1,657 cm$^{-1}$ to 1,602 cm$^{-1}$, aromatic 1,013 cm$^{-1}$.

Stage C: (17R) 11-beta-(4-chlorophenyl)-spiro(estra-4,9-dien-17,2'-(5H)-furan)-3-one The operation is done as at stage D of example 12, starting with 1.03 g of the product obtained in the preceding stage B, 20 cm³ of pyridine, 3 g of tosyl chloride and 25 cm³ of concentrated hydrochloric acid. 726 mg of the expected crystallized product is obtained. m.p. ≥ 260° C.

IR Spectrum (CHCl$_3$):

| dienone | 1,654 cm$^{-1}$ to 1,602 cm$^{-1}$ | |
| aromatic | 1,572 cm$^{-1}$, (shoulder) | 1,490 cm$^{-1}$. |
| $\langle$O$\rangle$ | 1,081 cm$^{-1}$ to 1,039 cm$^{-1}$. | |

Analysis: C$_{27}$H$_{29}$ClO$_2$ 420.98:

|  | C % | H % | S % |
|---|---|---|---|
| Calculated | 77.03 | 6.94 | 8.42 |
| Found | 77.0 | 6.9 | 8.2 |

EXAMPLE 15
(17R)-11-beta-[4-(1-methylethoxy)phenyl]-spiro(estra-4,9-dien-17,2'-(5H)-furan)-3-one Stage A: (Z) (1,2-ethanediyl) cyclic acetal of 5-alpha,17-beta-dihydroxy-11-beta-[4-(1-methylethoxy)phenyl]-17-alpha-3-(tetrahydro-2H-2-pyrannyloxy)-1-propenyl-estr-9-en-3-one The operation is done as in stage B of example 8, utilizing 2.5 g of the product obtained as indicated in stage A of example 8, 110 mg of cuprous chloride and 35 cm³ of the magnesium compound prepared as at example 3, starting with 1-bromo-4-(1-methylethoxy)-benzene. 6.764 g of crude product is obtained, which is chromatographed on silica (eluent: cyclohexane-ethyl acetate, 7-3, with 1% of triethylamine), and 3.173 g of the expected product is obtained.

IR Spectrum (CHCl$_3$):

|  | cm$^{-1}$ | cm$^{-1}$ | cm$^{-1}$ |
|---|---|---|---|
| OH in position 5 | 3,500 | | |
| Other OH | 3,602 to | 3,458 | shoulder |
| aromatic | 1,608 | 1,571 | 1,505 |

Stage B: (Z) 17-beta-hydroxy-17-alpha-(3-hydroxy-1-propenyl)-11-beta-[4-(1-methylethoxy)phenyl]-estr-4,9-dien-3-one The operation is done as at stage B of example 13, starting with, 314 g of the product obtained in the preceding stage A, 20 cm³ of ethanol and 2 cm³ of 2N hydrochloric acid. 1.257 g of the pure product expected is obtained.

IR Spectrum (CHCl$_3$):

|  | cm$^{-1}$ |
|---|---|
| OH, | 3,612 + combined |
| $\rangle$=O | 1,656 |
| $\rangle$C=C$\langle$ | 1,608 |
| aromatic | 1,585 (shoulder) 1,506 |

Stage C: (17R)-11-beta-[4-(1-methylethoxy)phenyl]-spiro(estra-4,9-dien-17,2'-(5H)-furan)-3-one The operation is done as at stage D of example 12, starting with, 1.22 g of product obtained at the preeding stage B, 20 cm³ of pyridine, 2.1 g of tosyl chloride and 25 cm³ of concentrated hydrochloric acid. 849 mg of pure product is obtained, which is crystallized form ethanol. m.p. 155° C.

IR Spectrum (CHCl$_3$):

|   | cm$^{-1}$ | cm$^{-1}$ | cm$^{-1}$ |
|---|---|---|---|
| dienone | 1,656 to | 1 608 | |
| aromatic | 1,506 | | |
| ⟨O⟩ (furan) | 1,806 to | 1,040 | |

Analysis: $C_{30}H_{36}O_3$ 444.619:

|   | C % | H % | S % |
|---|---|---|---|
| Calculated: | 81.04 | 8.16 | |
| Found: | 81.2 | 8.0 | |

EXAMPLE 16

(17R)
11-beta-[4-(1-pyrrolidinyl)phenyl]-spiro(estra-4,9-diem-17,2'-(5H)-furan)-3-one

Stage A: (Z) (1,2-ethanediyl) cyclic acetal of 5-alpha,17-beta-dihydroxy-11-beta-[4-(1-pyrrolidinyl)-phenyl]-17-alpha-[3-(1-tetrahydro-2H-2-pyrranyloxy)-1-propenyl]-estr-9-en-3-one The operation is done as at stage B of example 8, using 1.71 g of the product obtained at stage A of example 8, 180 mg of cuprous chloride and 20 cm³ of 4-(1-pyrrolidinyl)phenyl magnesium bromide, titrating 1M/l.

After extraction with either, washing with water and concentration under reduced pressur, 4.39 g of crude product is obtained which is chromatographed on silica (eluent: cyclohexane-ethyl acetate 7-3), and 2.3 g of the expected product is collected, which is used as it is for the following stage.

Stage B: (Z) 17-beta-hydroxy-17-alpha-(3-hydroxyprop-1-enyl)-11-beta-[4-(1-pyrrolidinyl)phenyl]-estr-4,9-dien-3-one.

2.3 g of the product prepared at stage A in 25 cm³ of methanol is agitated with 10 cm³ of 2N hydrochloric acid for two and a half hours at ambient temperature, then for 30 minutes at 50° C. The mixture is then cooled, diluted with water, alkalized by 20 cm³ of an N aqueous solution of sodium hydroxide, then with a solution of sodium acid carbonate. After extracting with ethyl acetate, washing with water, drying and eliminating the solvents under reduced pressure, 1.825 g of the expected product is obtained.

IR Spectrum (CHCl₃):

|   | cm$^{-1}$ | cm$^{-1}$ | cm$^{-1}$ |
|---|---|---|---|
| OH | 3,612 + combined | | |
| dienone | 1,054 | | |
| aromatic + –C=C | 1,614 | 1,559 | 1,518 |

Stage C: (17R) 11-beta-[1-pyrrolidinyl]-spiro(estra-4,9-diem-17,2'-(5H)-furan)-3-one The operation is done as in example 2, starting with 1.4 g of product obtained in the preceding stage B, 30 cm³ of pyridine, 3 g of tosyl chloride, and extracting with ether. 1.25 g of crude product is collected which is chromatographed on silica (eluting with cyclohexane-ethyl acetate 7-3, then with benzene-ethyl acetate 85-15). 0.9 g of the expected product is obtained.

IR Spectrum (CHCl₃):

|   | cm$^{-1}$ | cm$^{-1}$ | cm$^{-1}$ |
|---|---|---|---|
| dienone | 1,654 | | |
| C=C | 1,600 | | |
| aromatic bands | 1,614 | 1,519 | 1,517 |
| C—O—C, cyclic, | | 1,081 | 1,040 |

Analysis: $C_{31}H_{37}NO_2$ 455.64:

|   | C % | H % | S % |
|---|---|---|---|
| Calculated: | 81.72 | 8.18 | 3.07 |
| Found: | 81.6 | 8.2 | 3.0 |

EXAMPLE 17

(17R)
11-beta-(2-thienyl)-spiro(estra-4,9-dien-17,2'-(5H-furan-3-one

Stage A: (Z) (1,2-ethanediyl) cyclic acetal of 5-alpha,17-beta-dihydroxy-17-alpha-[3-(tetrahydro-2H-2-pyrannyloxy)-1-propenyl]-11-beta-(2-thienyl)-estr-9-en-3-one The operation is done as at stage B of example 8, starting with 2.5 g of the product prepared as at stage A of example 8, 110 mg of cuprous chloride and 22.2 cm³ of the magnesium compound prepared as at example 3, starting with 2-bromothiophene, titrating 1.05M/l.

3.6 g of crude product is obtained, which is chromatographed on silica, (eluting with cyclohexane and ethyl acetate 5-5), and 2.196 g of the expected product is collected.

IR Spectrum (CHCl₃): OH 3,600 cm$^{-1}$(f)+combined 3,500 cm$^{-1}$ thiophene 1,520 cm$^{-1}$ 852 cm$^{-1}$.

Stage B: (Z) 17-beta-hydroxy-17-alpha-(3-hydroxyl-1-propenyl)-11-beta-(2-thienyl)-estr-4,9-dien-3-one The operation is doen as at stage B of example 13, starting with 2.1 g of the product previously obtained, 20 cm³ of ethanol and 2 cm³ of 2N hydrochloric acid. 1.1 g of the expected pure product is obtained.

IR Spectrum (CHCl₃):

|   | cm$^{-1}$ | cm$^{-1}$ | cm$^{-1}$ |
|---|---|---|---|
| OH | 3,600 + combined | | |
| dienone | 1,658 | 1,604 | |
| thiophene | 1,520 | | |

Stage C: (17R) 11-beta-(2-thienyl-spiro(estra-4,9-dien-17,2'-(5H)-furan)-3-one The operation is done as at stage D of example 12, starting with 1.03 g of the product obtained in the preceding stage, 20 cm³ of pyridine, 2.1 g of tosyl chloride and 25 cm³ of concentrated hydrochloric acid. 984 mg of pure product is obtained which is crystallized from ethanol. m.p. 182° C.

IR Spectrum (CHCl₃):

|  | cm$^{-1}$ | cm$^{-1}$ | cm$^{-1}$ |
|---|---|---|---|
| dienone | 1,658(F) to | 1,604 |  |
| ⌐O⌐ (furan ring) | 1,081 | 1,041 |  |
| thiophene | 1,520 |  |  |

Analysis: $C_{25}H_{28}SO_2$:

|  | C % | H % | S % |
|---|---|---|---|
| Calculated: | 76.49 | 7.19 | 8.16 |
| Found: | 76.4 | 7.3 | 8.1 |

EXAMPLE 18

(17R) 11-beta-[4-(ethylthio)phenyl]-spiro(estra-4,9-dien-17,2'-(5H)-furan)-3-one Stage A: (Z) (1,2-ethanediyl) cyclic acetal of 5-alpha,17-beta-dihydroxy-11-beta-[4-(ethylthio)-phenyl]-17-alpha-[3-(1-tetrahydro-2H-2-pyrannyl-oxy)-1-propenyl-estr-9-en-3-one.

Preparation of the magnesium compound

The operation is done as at example 3, starting with 1.125 g of magnesium and 9.3 g of 1-bromo-4-ethylthio benzene and obtaining a solution of the magnesium compound titrating 0.87 M/l.

Condensation

The operation is done as at stage B of example 8, utilizing 3 g of the product obtained at stage A of example 8, 110 mg of cuprous chloride and 30 cm$^3$ of the magnesium compound prepared above. After extraction with methylene chloride, washing, drying and elimination of the solvents under reduced pressure, 10 g of the crude prodcut is obtained which is chromatographed on silica (eluent:: cyclohexane-ethyl acetate 5-5), and 3.519 g of the expected product is collected.

IR Spectrum (CHCl$_3$):

|  | cm$^{-1}$ | cm$^{-1}$ | cm$^{-1}$ |
|---|---|---|---|
| OH | 3,600 + associated |  | 3,452 |
| aromatic | 1,592 (f) | 1,575 (f) | 1,492 (F) |

Stage B: (Z) 11-beta-[4-(ethylthio)phenyl]-17-beta-hydroxy-17-alpha-(3-hydroxy-1-propenyl)-estra-4,9-dien-3-one 3.474 g of the product obtained at the preceding stage is agitated for 30 minutes in 60 cm$^3$ of methanol with 2 cm$^3$ of methylene chloride and 5 cm$^3$ of 2N hydrochloride acid. After concentrating this to a small volume, 10 cm$^3$ of an N aqueous solution of sodium hydroxide is added, followed by extraction with methylene chloride. The extracts are washed with water, dried, the solvents are eliminated under reduced pressure, and 2.574 g of crude product is obtained which is chromatographed on silica (eluent: cyclohexane-ethyl acetate 3-7), and the residue obtained is crystallized form ethanol. 1.052 g of the expected pure product is collected. m.p. about 100° C.

IR Spectrum (CHCl$_3$):

|  | cm$^{-1}$ | cm$^{-1}$ | cm$^{-1}$ |
|---|---|---|---|
| OH | 3,615 + combined |  |  |
| C═O | 1,654 |  |  |
| —C═C— | 1,601 | 1,556 (f) | 1,492 |

Stage C: (17R)-11-beta-[4-(ethylthio)phenyl]-spiro(estra-4,9-dien-17,2'-(5H)-furan)-3-one The operation is done as in example 12 stage D, starting with 600 mg of the product obtained in the preceding stage, 15 cm$^3$ of pyridine, 1.5 g of tosyl chloride.

872 mg of crude product is obtained which is chromatographed on silica (eluent: cyclohexane-ethyl acetate 5-5), and crystallized from ethanol. m.p. 100° C.

IR Spectrum (CHCl$_3$):

|  | cm$^{-1}$ | cm$^{-1}$ |
|---|---|---|
| ketone conjugated aromatic | 1,654 to 1,558 | 1,601 1,492 |
| ⌐O⌐ (furan ring) | 1,081 |  |

Analysis: $C_{30}H_{34}O_2S$ 446.657:

|  | C % | H % | S % |
|---|---|---|---|
| Calculated: | 77.98 | 7.67 | 7.19 |
| Found: | 77.9 | 7.7 | 7.1 |

EXAMPLE 19

(17R) 11-beta-[4-(4,5-dihydro-4,4-dimethyl-2-oxazolyl)-phenyl]-spiro(estra-4,9-dien-17,2'-(5H)-furan)-3-one Stage A: (Z) (1,2-ethanediyl) cyclic acetal of 11-beta-[4-(4.5-dihydro-4,4-dimethyl-2-oxazolyl-phenyl]-5-alpha,17-beta-dihydroxy-17-alpha-[3-tetrahydro-2H-2-pyrannyloxy)propenyl]-estr-9-en-3-one Preparation of magnesium compound The operation is done as in example 3, starting with 3.5 g of magnesium and 25 g of 2-(4-bromophenyl-4,5-dihydro-4,4-dimethyl oxazole, and obtaining a solution titrating 0.74M/l.

Condensation

The operation is done as at example 3, starting with 80 cm$^3$ of the above magnesium compound solution, 800 mg of cuprous chloride and 10 g of the product prepared as at stage A of example 8. After chromatography on silica (eluent: cyclohexane-ethyl acetate 3-7), 14.3 g of the expected product is obtained, used as it is for the following stage IR Spectrum (CHCl$_3$):

|  | cm$^{-1}$ | cm$^{-1}$ | cm$^{-1}$ |
|---|---|---|---|
| 17-OH | 3,605 + combined |  | 3,420 |

43

-continued

|  | cm$^{-1}$ | cm$^{-1}$ | cm$^{-1}$ |
|---|---|---|---|
| 5-OH | 3,505 | | |
| C=N | 1,646 | | |
| aromatic | 1,609 | 1,563 | 1,509 |

Stage B: (Z) 11-beta-[4-(4,5-dihydro-4,4-dimethyl-2-oxazolyl)-phenyl]-17-beta-hydroxy-17-alpha-(3-hydroxy-1-propenyl)-estra-4,9-dien-3-one Under an inert atmosphere, 13.1 g of the preceding product is dissolved in 130 cm³ of dioxan and 130 cm³ of 2N hydrochloric acid, with agitation for 1 hour. The solution is then poured into an aqueous solution of sodium bicarbonate and extracted with ethyl acetate. The extracts are washed with water, dried and the solvents are eliminated under reduced pressure. 10.3 g of crude product is obtained which is recrystallized from ether. m.p. 269° C.

IR Spectrum (CHCl₃):

|  | cm$^{-1}$ | cm$^{-1}$ | cm$^{-1}$ |
|---|---|---|---|
| C=O + C=N | 1,648 | | |
| C=C dienone } aromatic | about 1,603 | | |
| aromatic bands | 1,563 to 1,510 | | |

Stage C (17R) 11-beta-[4-(4,5-dihydro-4,4-dimethyl-2-oxazolyl)-phenyl]-spiro(estra-4,9-dien-17,2'-(5H))-furan)-3-one 0.49 g of the product obtained previously is put into suspension in 10 cm³ of pyridine, 1 g of tosyl chloride is added, and the whole is agitated for 2 hours and a half. After diluting with iced water, the precipitate is separated and dissolved in methylene chloride. The organic phase is separated, dried and the solvents are eliminated under reduced pressure. The residue is chromatographed on silica (eluent: methylene chloride - ethyl acetate 1-1), and 0.41 g of the expected product is obtained. m.p. 250° C.

IR Spectrum (CHCl₃):

|  | cm$^{1}$ | cm$^{-1}$ | cm$^{-1}$ |
|---|---|---|---|
| C=O + C=N | 1,648 | | |
| C=C dienone } aromatic | 1,603 | 1 564 | 1 509 |
| CO=C | 1,080 | | |

Analysis : C₃₂H₃₇NO₃ 483.65:

|  | C % | H % | N % |
|---|---|---|---|
| Calculated: | 79.47 | 7.71 | 2.89 |
| Found: | 79.5 | 7.8 | 2.8 |

44

EXAMPLE 20

(17R) 11-[4-[2-(dimethylamino)ethoxy]phenyl]-spiro-(estra-4,9-dien-17,2'-(5H)-furan)-3-one Stage A: (Z) (1,2-ethanediyl) cyclic acetal of 5-alpha,17-beta-dihydroxy-11-beta-[4-[2-(dimethylamino)ethoxy]phenyl]-17-alpha-[3-(tetrahydro-(2H)-2-pyrannyloxy)-1-propenyl]-estra-9-en-3-one The operation is done as at stage B of example 8 utilizing at the start 75.5 cm³ of a magnesium compound solution prepared from 4-(N,N-dimethylaminoethoxy)-bromobenzene titrating 0.7M/1, 0.25 g of cuprous chloride and 5 g of the product prepared as at stage A of example 8. After chromatography on silica, (eluent: ethyl acetate - triethylamine 93-2), 2.620 g of the expected product is obtained.

IR Spectrum (CHCl₃):

|  | cm$^{-1}$ | cm$^{-1}$ | cm$^{-1}$ |
|---|---|---|---|
| $-N\begin{smallmatrix}C\\C\end{smallmatrix}$ | 2,780 | | |
| aromatic | 1,609 | 1,581 | 1,508 |

Stage B: (Z) 11-beta-[4-[2-(dimethylamino)ethoxy]phenyl]-17-beta-hydroxy-17-alpha-[3-hydroxy-1-propenyl]-estra-4,9-dien-3-one A solution comprising 2.62 g of the product obtained above in 13 cm³ of ethanol is cooled to 0° C., and 7.9 cm³ of 2N hydrochloric acid is added, with agitation for 30 minutes. 6 cm³ of ammonium hydroxide and 25 cm³ of water are added, with further agitation for 30 minutes. The precipitate formed is separated and dissolved in methylene chloride, dried and concentrated to dryness under reduced pressure. 1.948 g of crude product is obtained which is chromatographed on silica (eluent: ethyl acetate - triethylamine, 8-2), then the residue is recrystallized from isopropanol. m.p. 136° C.

IR Spectrum (CHCl₃):

|  | cm$^{-1}$ | cm$^{-1}$ | cm$^{-1}$ | cm$^{-1}$ |
|---|---|---|---|---|
| OH | 3,613 | | | |
| dienone | 1,656 | to 1,608 | | |
| aromatic | 1,582 | shoulder, | 1,508 (F), | 832 (def) |

Stage C: (17R) 11-beta-[4-[2-(dimethylamino)ethoxy]phenyl]-spiro(estra-4,9-dien-17,2'-(5H)-furan)-3-one The operation is done as at stage D of example 12, starting with 2,268 g of the product prepared in the preceding stage B, 45 cm³ of tosyl chloride and 45 cm³ of 6N hydrochloric acid. After chromatography (eluent: ethyl acetate - triethylamine 95-5) and crystallization from isopropanol, 0.815 g of the expected product is obtained. m.p. 136° C.

[alpha]$_D$= +156.5°±3°. (c=0.6% CHCl₃).

IR Spectrum (CHCl₃):

| | cm$^{-1}$ | cm$^{-1}$ |
|---|---|---|
| C=O | 1,656 | |
| C=C | 1,580 | |
| aromatic | 1,608 | 1,508 |

EXAMPLE 21

(17R) 11-beta-[4-[2-(methylthio)ethoxy]phenyl]-spiro(estra-4,9-dien-17,2'-(5H)-furan-3-one Stage A: 1,2-ethanediyl cyclic acetal of 5-alpha, 17-beta-dihydroxy-11-beta-[4-[2-(methylthio)ethoxy]phenyl]-17-alpha-[3-(1-tetrahydro-(2H)-2-pyrannyloxy)-1-propenyl]-estra-9-en-3-one Preparation of the magnesium compound The operation is done as in example 3, utilizing 0.8 g of magnesium and 6.1 g of 4-bromo-2-[(methylthio)ethoxy]benzene. A solution titrating 0.59M/l is obtained.

Condensation

The operation is done as at stage B of example 8, from 0.472 g of the product prepared as in stage A of example 8, 22 mg of cuprous chloride and 8.3 cm³ of the magnesium compound solution prepared above. 0.46 g of the expected product is obtained.

IR Spectrum (CHCl₃):

| | cm$^{-1}$ | cm$^{-1}$ | cm$^{-1}$ |
|---|---|---|---|
| 17-OH + combined | 3,400 | | |
| 5-OH | 3,505 | | |
| aromatic | 1,608 | 1,580 | 1,507 |

The 4-bromo-2-[(methylthio)ethoxy]benzene utilized at the start of stage A has been prepared as follows.

Under an inert atmosphere, 73.9 g of parabromophenol is dissolved in 430 cm³ of a normal aqueous solution of sodium hydroxide; over 5 minutes, 47.3 g of 2-chloroethylmethyl sulphide is added, and the mixture is heated for 18 hours at reflux. It is then cooled, the sodium chloride formed is separated, washed with ethanol, dried, and the solvents are eliminated under reduced pressure. The residue is taken up with water, extracted with ether, the organic phase is washed with a normal aqueous solution of sodium hydroxide, then with water, dried and evaporated to dryness. The residue is chromatographed on siliva (eluent: hexane-ethyl acetate 95-5), and 87 g of the expected product is collected, used as it is for the preparation of the magnesium compound.

Stage B: 17-beta-hydroxy-17-alpha-(3-hydroxypropenyl)-11-beta-[4-[2-(methylthio)ethoxy]phenyl]-estra-4,9-dien-3-one The operation is done as at stage B of example 18, using 2.75 g of the product prepared in the preceding stage A, 60 cm³ of methanol, 10 cm³ of methylene chloride and 6 cm³ of 2N hydrochloric acid. After chromatography on silica (eluent: methylene chloride - acetone, 85-15), 3 g of product is obtained which is used as it is for the following stage.

IR Spectrum (CHCl₃):

| | cm$^{-1}$ | cm$^{-1}$ | cm$^{-1}$ |
|---|---|---|---|
| C=O | 1,710 | | |
| aromatic | 1,607 | 1,507 (F) | 1,572 (f) |

Stage C: (17R) 11-beta-[4-[2-methylthio)ethoxy]phenyl]-spiro(estra-4,9-dien-17,2'-(5H)-furan-3-one The operation is done as at stage D of example 12, starting with 1.4 g of the product prepared above, 28 cm³ of pyridine, 2.26 g of tosyl chloride and 28 cm³ of 6N hydrochloric acid. 1.82 g of the expected product is obtained, crystallized.

[alpha]$_D$ = +184.5°±2° (c=1% CHCl₃).

IR Spectrum (CHCl₃):

| | cm$^{-1}$ | cm$^{-1}$ |
|---|---|---|
| C=O | 1,656 | |
| C=C | 1,608 | 866 (def) |
| aromatic | 1,508 | |
| C—O—C | 1,082 to | 1,042 |

Analysis: C₃₀H₃₆O₃S:

| | C % | H % | S % |
|---|---|---|---|
| Calculated: | 74.42 | 7.89 | 6.39 |
| Found: | 74.5 | 7.9 | 6.4 |

EXAMPLE 22

(17R) 11-beta-(3-methoxyphenyl)-spiro(estra-4,9-dien-17,2'-(5H)-furan)-3-one

Stage A: (Z) 3,3-dimethoxy ketal of 5-alpha,17-beta-dihydroxy-11-beta-(3-methoxyphenyl)-17-alpha-[3-(tetrahydro-2H-2-pyrannyloxy)-1-propenyl]-estra-9-en-3-one The operation is done as in example 5 C, starting with 3 g of the product prepared as in example 5 B, 100 mg of cuprous chloride and 19 cm³ of the magnesium compound solution prepared from 3-bromo anisole, titrating 1M/l. After chromatography on silica (eluent: cyclohexane-ethyl acetate, 7-3 with 1% of triethylamine), 1.522 g of the expected product is obtained.

Stage B: (Z) 11-beta-(3-methoxyphenyl)-17-beta-hydroxy-17-alpha-(3-hydroxy-1-propenyl)-estra-4,9-dien-3-one The operation is done as in example 5 D, with 1.5 g of the product obtained in the previous stage and 1.5 g of potassium hydrogen sulphate. After chromatography on silica (eluent: n-hexane - ethyl acetate 7-3), 0.8 g of the expected product is obtained. m.p. 167°-168° C.

IR Spectrum (CHCl₃):

| | cm$^{-1}$ | cm$^{-1}$ | cm$^{-1}$ |
|---|---|---|---|
| OH | 3,613 + combined | | |
| dienone | 1,656 | 1,603 | |
| aromatic | 1,598 | 1,583 | 1,487 |

Stage C: (17R) 11-beta-(3-methoxyphenyl)-spiro(estra-4,9-dien-17,2'-(5H)-furan)-3-one The operation is done as at stage E of example 5, using 0.77 g of the product prepared in the preceding stage B, 20 cm³ of pyridine, 2.7 g of tosyl chloride and 25 cm³ of concentrated hydrochloric acid. After chromatography on silica (eluent: cyclohexane-ethyl acetate, 5-5), 0.624 g of the expected product is obtained, which is crystallized from ethanol. m.p. 170° C.

IR Spectrum (CHCl₃):

|  | cm⁻¹ | cm⁻¹ | cm⁻¹ |
|---|---|---|---|
| C=O | 1,656 (F) | | |
| C=C aromatic | 1,604 | 1,598 | 1,583 |
| C—O—C 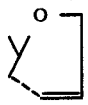 | 1,080 to | 1,040 | |

Analysis: C₂₈H₃₂O₀ 416,565:

|  | C % | H % |
|---|---|---|
| Calculated: | 80.73 | 7.74 |
| Found: | 80.4 | 7.9 |

EXAMPLE 23

(17R) 11-beta-(4-methoxyphenyl)-spiro(estra-4,9-dien-17,2'-(5H)-furan)-3-one

Stage A: (Z) dimethoxy-ketal of 5-alpha,17-beta-dihydroxy-11-beta-(4-methoxyphenyl)-17-alpha-[3-(tetrahydro-2H-2-pyrannyloxy)-1-propenyl]-estr-9-en-3-one The operation is done as in stage C of example 5, utilizing at the start 3 g of the product prepared in stage B of example 5, 190 mg of cuprous chloride and 19 cm³ of the magnesium compound solution prepared starting with 4-bromo anisole and titrating 1M/l. After chromatography on silica (eluent: petroleum ether (b.p. 40°-60° C.) and ethyl acetate, 7-3, with 1% triethylamine), 1.078 g of the expected product is obtained and 0.625 g of the corresponding isomer 5-beta-hydroxy-11-alpha-(4-methoxyphenyl).

Stage B: (Z) 17-beta-hydroxy-17-alpha-(3-hydroxy-1-propenyl)-11-beta-(4-methoxyphenyl)-estra-4,9-dien-3-one The operation is done as in example 5, stage D, starting with 1 g of the product prepared in the preceding stage A and 1 g of potassium hydrogen sulphate. 736 mg of crude product is obtained which is utilized as it is in the following stage.

Stage C: (17R) 11-beta-(4-methoxyphenyl)-spiro(estr-4,9-dien-17,2'-(5H)-furan)-3-one The operation is done as in Stage E of example 5, starting from 736 mg of the product obtained from the preceding stage, 20 cm³ of pyridine, 2.1 g of tosyl chloride and 25 cm³ of concentrated hydrochloric acid. After chromatography on silica (eluent: cyclohexane and ethyl acetate, 7-3), 383 mg of the expected product is obtained, which is crystallized from ethanol. m.p. 185° C.

IR Spectrum (CHCl₃):

|  | cm⁻¹ | cm⁻¹ | cm⁻¹ |
|---|---|---|---|
| dienone | 1,656 to | 1,607 | 864 |
| aromatic | 1,582 | 1,509 | |
| O ring | 975 to | 1,080 | |

EXAMPLE 24

(17R) 4',5'-dihydro-11-beta-[2,3-dihydro-1-methyl-(1H)-indol-5-yl]-spiro(estra-4,9-dien-17,2'-(3H)-furan)-3-one Stage A: (1,2-ethanediyl) cyclic acetal of 5-alpha,17-beta-dihydroxy-11-beta-[2,3-dihydro-1-methyl(1H)-indol-5-yl]-17-alpha-[3-(tetrahydro-(2H)-pyrannyloxypropyl)-estra-9-en-3-one The operation is done as in stage B of example 12, using at the start 2.45 g of the product prepared as in stage A of example 12, 110 mg of cuprous chloride and 35 cm³ of magnesium compound solution prepared as in example 3, starting with 5-bromo-2-methyl indoline and titrating 0.6M/l. 1.218 g of the expected product is obtained.

IR Spectrum (CHCl₃):

|  | cm⁻¹ | cm⁻¹ | cm⁻¹ |
|---|---|---|---|
| 5-OH | 3,500 | | |
| OH—C—CH₂— | doublet | 3,615 | 3,593 |
| aromatic | 1,612 to | 1,496 | |

Stage B: 17-beta-hydroxy-17-alpha-(3-hydroxypropyl)-11-beta[2,3-dihydro-1-methyl-(1H)-indol-5-yl) estra-4,9-dien-3-one The operation is done as in stage C of example 12, starting with. 3.025 g of the product prepared as indicated in the preceding stage, 30 cm³ of ethanol and 5 cm³ of 2N hydrochloric acid. 1.658 g of the expected product is recovered.

IR Spectrum (CHCl₃):

|  | cm⁻¹ | cm⁻¹ |
|---|---|---|
| OH free | 3,619 | + combined |
| ketone conjugated | 1,655 | |
| aromatic | 1,611 to | 1,497 |

Stage C: (17R) 4',5'-dihydro-11-beta-[2,3-dihydro-1-methyl-(1H)-indol-5-yl]-spiro(estra-4,9-dien-17,2'-(3H)-furan)-3-one The operation is done as in stage D of example 12, starting with 1.658 g of product prepared at stage B, 20 cm³ of pyridine, 2.1 g of tosyl chloride and 20 cm3 of concentrated hydrochloric acid. After chromatography on silica (eluent: cyclohexane-ethyl acetate 7-3), 0.729 of the expected pure product is obtained.

IR Spectrum (CHCl₃:

|  | cm⁻¹ | cm⁻¹ |
|---|---|---|
| ketone conjugated | 1,633 | |
| aromatic + C=C | 1,602 | 1,497 |

 probable

Analysis: C₃₀H₃₇NO₂ 443.634:

|  | C % | H % | N % |
|---|---|---|---|
| Calculated: | 81.22 | 8.41 | 3.16 |
| Found: | 81.0 | 8.6 | 3.1 |

EXAMPLE 25

(17R) 4'5'-dihydro-11)-beta-[4-[(3-methylbutyl)thio]-phenyl]-spiro(estra-4,9-dien-17,2'-(3H)-furan)-3-one

Stage A: (1,2-ethanediyl) cyclic acetal of 5-alpha-17-beta-dihydroxy-11-beta-[4-[(3-methylbutyl)thio]thio]-17-alpha-[3-(tetrahydro-2H-2-pyrannyloxy)-propyl]- estr-9-en-3-one The operation is done as in stage B of example 12, starting with 3.5 g of the product prepared in stage A of example 12, 1.24 g of cuprous chloride and 22 cm³ of a magnesium compound solution prepared as in example 3, from 4-[(3-methyl)butylthio] bromobenzene and titrating 1.05 M/l.

After chromatography on silica (eluent:methylene chloride-acetone 95-5 with 1% of triethylamine), 4.08 g of the expected product is obtained.

IR Spectrum (CHCl₃):

|  | cm⁻¹ | cm⁻¹ | cm⁻¹ |
|---|---|---|---|
| OH | 3,620 to | 3,597 | + combined. |
| aromatic | 1,594 (f) | 1,552 (f) | 1,492 (f) |

Stage B: 17-beta-hydroxy-17-alpha-(3-hydroxypropyl)-11-beta-[4-[(3-methylbutyl)thio]phenyl]-estra-4,9-dien-3-one The operation is done as in stage B of example 16, starting with 4.05 g of the product prepared above, 30 cm³ of methanol, and 12 cm³ of 2N hydrochloric acid. 3.34 g of crude product is obtained which is chromatographed on silica (eluent: methylene chloride and ethyl acetate, 3-7), and 2.3 g of the expected pure product is recovered.

IR Spectrum (CHCl₃):

|  | cm⁻¹ | cm⁻¹ |
|---|---|---|
| OH free | 3,620 + | combined |
| dienone | 1,654 | 1,601 |
| aromatic | 1,554 to | 1,492 |

Stage C: (17R) 4'5'-dihydro-11-beta-[4-[(3-methylbutyl)thio]-phenyl]-spiro(estra-4,9-dien-17,2'-(3H)-furan)-3-one The operation is done as in example 2, starting with 2.3 g of the product obtained above, 45 cm³ of pyridine and 4.3 g of tosyl chloride.

2.14 g of crude product is obtained which is purified by recrystallization from ethanol. m.p. 200° C.

IR Spectrum (CHCl₃):

|  | cm⁻¹ | cm⁻¹ | cm⁻¹ |
|---|---|---|---|
| C=O | 1,653 | | |
| —C=C aromatic | 1,602 | 1,555 (f) | 1,492 (f) |
| C—O—C | | 1,078 to 1,055 | |

EXAMPLE 26

(17R) 4',5'-dihydro-11-beta-[4-(1-pyrrolidinyl)phenyl]-spiro(estra-4,9-dien-17,2'-(3H)-furan)-3-one

Stage A: (1,2-ethanediyl) cyclic acetal of 5-alpha-18-beta-dihydroxy-11-beta-[4-[4-(1-pyrrolidinyl)phenyl)]-17-alpha-[3-[(2-tetrahydropyrannyl)-oxy]-1-propynyl]-estr-9-en-3-one The operation is done as in stage B of example 3, starting with 3.5 g of the product prepared as in stage A of example 3, 73 mg of cuprous chloride and 23 cm³ of magnesium compound solution prepared as indicated in example 3, starting with N-(4-bromophenyl) pyrrolidine and titrating 1.3 M/l.

After chromatography on silica (eluent:methylene chloride and acetone, 92-8, with 1% of triethylamine, then ethyl acetate and n-hexane, 5—5, with 2% of triethylamine) 3.52 g of the expected pure product is obtained.

IR Spectrum (CHCl₃):

|  | cm⁻¹ | cm⁻¹ | cm⁻¹ |
|---|---|---|---|
| 17-OH | 3,599 | | |
| 5-OH | 3,508 | | |
| aromatic | 1,615 | 1,599 | 1,517 |

Stage B: (1,2-ethanediyl) cyclic acetal of 5-alpha-17-beta-dihydroxy-11-beta-[4(1-pyrrolidinyl)-phenyl]-17-alpha[3-[(2-tetrahydropyrannyl)-oxy]-propyl]-ester-9-en-3-one The operation is done as in example 4, stage A, starting with 2.62 g of the product prepared above, dissolved in 172 cm³ of a (1—1) solution of benzene and ethanol and with 1.048 g of Wilkinson's reagent, hydrogenating for 4 hours 45 minutes.

2.1 g of the expected product is obtained.

IR Spectrum (CHCl₃):

|   | cm$^{-1}$ | cm$^{-1}$ | cm$^{-1}$ |
|---|---|---|---|
|  OH, CH2 | doublet | 3,620 | 3,600 |

|   | cm$^{-1}$ |   |   |
|---|---|---|---|
| 5-OH | 3,505 | | |
| aromatic | 1,614 to | 1,517 | |

Stage C:
17-beta-hydroxy-17-alpha-(3-hydroxypropyl-11-beta-[4-(1-pyrrolidinyl)phenyl]-estra-4,9-dien-5-one The operation is done as at stage B of of example 4, starting with 2.09 g of the product obtained above, 32 cm$^3$ of methanol and 10.45 cm$^3$ of 2N hydrochloric acid.

After chromatography on silica (eluent:methylene chloride and methanol, 95-5, with 2% of triethylamine), 1.31 g of the expected product is obtained.

IR Spectrum (CHCl$_3$):

|   | cm$^{-1}$ | cm$^{-1}$ |   |
|---|---|---|---|
| dienone | 1,654 to | 1,590 | |
| aromatic | 1,614 | 1,559 | 1,518 |
| OH | 3,620 + combined. | | |

Stage D: (17R)
4',5'-dihydro-11-beta-[4-(1-pyrrolidinyl)phenyl]-spiro(estra-4,9-dien-17,2'-(3H)-furan)-3-one The operation is done as at stage C of example 4, starting with 1.28 g of the product obtained in the preceding stage, 20 cm$^3$ of pyridine and 2.6 g of tosyl chloride After chromatography on silica (eluent:cyclohexane and ethyl acetate, 75-25 with 2% of triethylamine), 0.73 g of the expected product is obtained.

IR Spectrum (CHCl$_3$)

|   | cm$^{-1}$ | cm$^{-1}$ | cm$^{-1}$ |
|---|---|---|---|
| dienone | 1,653 (f) | | |
| C=C | 1,600 (shoulder) | | |
| aromatic | 1,614 (F) | 1,559 | 1,518 (F) |

Analysis: C$_{31}$H$_{39}$NO$_2$ 457.66:

|   | C% | H% | N% |
|---|---|---|---|
| Calculated (solvatation 12% cycohexane | 81.86 | 9.27 | 2.69 |
| Found | 81.6 | 9.4 | 2.6 |

EXAMPLE 27
(17R)
11-beta-[4-methylthio)phenyl]-spiro(estra-1,3,5(10)-trien-17,2'-(5H)-furan)-3-ol

1. Formation of phenol acetate 0.5 g of product prepared at example 3E in solution in 10 cm$^3$ of methylene chloride is cooled to +3° C., then 0.5 cm$^3$ of acetic anhydride is added drop by drop, followed by 0.25 cm$^3$ of acetyl chloride, with agitation for 50 minutes. The reactional medium is diluted with 20 cm$^3$ of iced water, 5 cm$^3$ of an N aqueous solution of sodium hydroxide is added, with agitation for 30 minutes. After extraction with methylene chloride, the organic phase is washed, dried and the solvents are eliminated under reduced pressure. 0.548 g of crude product is obtained, which is chromatographed on silica (eluent: n-hexane-ethyl acetate, 7-3), and 0.241 g of the expected acetate is recovered.

2. Saponification

The product obtained above is taken up in 3 cm$^3$ of ethanol, 4 drops of an N aqueous solution of sodium hydroxide are added, and after agitation and dilution with 10 cm$^3$ of water, the precipitate is filtered off, washed, then dried under reduced pressure. The residue is purified by chromatography on silica (eluent: n-hexane and ethyl acetate, 8-2). 0.205 g of the expected product is obtained.

IR Spectrum (CHCl$_3$):

|   | cm$^{-1}$ | cm$^{-1}$ | cm$^{-1}$ |
|---|---|---|---|
| OH | 3,600 | | |
| aromatic | 1,602 | 1,582 | 1,434 |

EXAMPLE 28
(17R)
11-beta-[4-[2-(methylthio)ethoxy]phenyl]-spiro(estra-1,3,5(10)-trien-17,2'-(5H)-furan)-3-ol and its acetate and
(17R)
11-beta-[4-[2-(methylthio)ethoxy]phenyl]-spiro[estra-5(10)-9(11)-dien-17,2'-(5H)-furan)-3-one

1. Formation of the phenol acetate

A solution comprising 1 g of product obtained at example 21 in 20 cm$^3$ of methylene chloride is cooled to about +5° C., 1 cm$^3$ of acetic anhydride and 0.5 cm$^3$ of acetyl bromide are added, then the temperature is allowed to return to the ambient. After agitating for 50 minutes, the reactional medium is poured into an iced solution of sodium bicarbonate, agitated for 10 minutes, then extracted with methylene chloride. The organic phases are separated, washed with water, dried, and the solvents are eliminated under reduced pressure. The residue is chromatographed on silica (eluent, hexane-ethyl acetate, 80-20, then 85-15). 0.509 g of the acetate (17R) 11-beta-[4-[2-(methylthio)ethoxy]phenyl]-spiro-(estra-1,3,5(10)-trien-17,2'-(5H)-furan)-3-ol is obtained.

IR Spectrum (CHCl$_3$):

|   | cm$^{-1}$ | cm$^{-1}$ | cm$^{-1}$ |
|---|---|---|---|
| C=O | 1,746 | | |
| presence of O, RO | | | |
| average band | 1,664 | | | in addition, 90 mg of (17R) 11-beta-[4-[2-(methylthio)ethoxy]phenyl]-spiro(estra-5-(10)-9)11)dien-17,2'-(5H)-furan-3-one is obtained.

IR Spectrum (CHCl$_3$):

|  | cm⁻¹ | cm⁻¹ | cm⁻¹ |
| --- | --- | --- | --- |
| C=O | 1,711 | | |
| C—C aromatic | 1,607 | 1,507 | |

2. Saponification 0.5 g of the above phenol acetate is taken up in 7.5 cm³ of methanol and 1 cm³ of methylene chloride, then, drop by drop, 0.5 cm³ of sodium hydroxide is added, with agitation for 20 minutes at ambient temperature. The reactional mixture is then diluted with hydrochloric acid and extracted with methylene chloride. The extracts are washed with water, dried and the solvents are eliminated under reduced pressure, then the residue is chromatographed on silica (eluent: hexane and ethyl acetate, 8-2, then emthylene chloride) and 354 mg of the expected (17R) 11-beta-[4-[2-(methylthio)-ethoxy]-phenyl]-spiro(estra-1,3,5(10)-trien-17,2'-(5H)-furan)-3-ol is obtained, which is recrystallized from isopropanol. m.p. 198° C.

IR Spectrum (CHCl₃):

|  | cm⁻¹ | cm⁻¹ | cm⁻¹ |
| --- | --- | --- | --- |
| OH phenolic, aromatic | 3,599 1,610 | 1,582 | 1,511 |
| C—O—C | 1,086 to | 1,037 | |

[alpha]$_D$: −84.5°+ ±1.5° (c=0.8% CHCl₃).

EXAMPLE 29

(17R) 2-beta-methyl-11-beta-[4-(methylthio)phenyl]-spiro(estra-4,9-diene-17,2'-(5H)-furan)-3-one and the corresponding 2-alpha isomer, and (17R) 2,2-dimethyl-11-beta-[4-(methylthio)phenyl]-spiro(estra-4,9-dien-17,2'-(5H)-furan)-3-one Under an inert atmosphere, 2.45 cm³ of n-butyl-lithium in solution in hexane (1.6M) and 5 cm³ of tetrahydrofuran are cooled to −65°/−70° C., and, over 20 minutes, 0.66 cm³ of cyclohexylisopropylamine in 5 cm³ of tetrahydrofuran is added: after agitating for 15 minutes, over 30 minutes, 1.4 g of (17R) 11-beta-[4-(methylthio)phenyl]-spiro(estra-4,9-dien-17,2'-(5H)-furan)-3-one obtained at example 3, in suspension in 15 cm³ of tetrahydrofuran, is added, with agitation for 15 minutes, followed by adding 0.4 cm³ of methyl iodide. The temperature is allowed to return to the ambient, with agitation for 1 hour, then 20 cm³ of an aqueous solution of ammonium chloride is added. After decanting, the organic phase is washed with salted water, extraction is done again with ethyl acetate, the extracts are dried and concentrated to dryness. 1.5 g of crude product is obtained which is chromatographed on silica, eluting with a mixture of petroleum ether (b.p. 40°/70° C.) and ehtyl acetate, 9-1).

There is obtained:

290 mg of isomer (17R) 2-beta-methyl-11-[4-(methylthio)phenyl]-spiro(estra-4,9-diene-17,2'-(5H)-furan)-3-one, which is recrystallized from isopropyl ether, m.p. 176° C., 355 mg of the 2-alpha-methyl isomer, which is recrystallized from isopropyl ether, m.p. 164° C., and 65 mg of (17R) 2,2-dimethyl-11-beta-[4-(methylthio)phenyl]-spiro-(estra-4,9-dien-17,2'-(5H)-furan)-3-one.

IR Spectrum (CHCl₃):

| 2-beta-methyl isomer | C=O, 1,656 cm⁻¹, C=C, 1,605 and 865 cm⁻¹ |
| --- | --- |
| 2-alpha-methyl isomer | C=O, 1,654 cm⁻¹, C=C complex, max. 1,595 cm⁻¹ aromatic, 1492 cm⁻¹ shoulder 1,607 cm⁻¹ |
| 2,2-dimethyl product | C=O, 1,651 cm⁻¹, C=C, 1,603 cm⁻¹ aromatic, 1,492 cm⁻¹. |

EXAMPLE 30

(E) (17R) oxime of 11-beta-[4-(methylthio)phenyl]-spiro(estra-4,9-dien-17,2'-(5H)-furan)-3-one and the corresponding (Z) isomer Under an inert atmosphere, 1.36 g of (17R) 11-beta-[4-(methylthio)phenol]-spiro(estra-4,9-dien-17,2'-(5H)-furan)-3-one, obtained at example 3 is heated to reflux for 75 minutes in 14 cm³ of ethanol, with 2.6 cm³ of pyridine and 0.44 g of hydroxylamine hydrochloride. After allowing the temperature to return to ambient, the reactional medium is poured into 100 cm³ of water, then extracted with ethyl acetate. The organic phase is washed, dried, and concentrated to dryness under reduced pressure. 1.47 of crude product is obtained which is chromatographed on silica, eluting with a mixture of petroleum either (b.p. 40°/70° C.) and ethyl acetate, 8-2.

805 mg of isomer (E) is recovered and is dissolved hot in methylene chloride and recrystallized from isopropyl ether, m.p. 250° C., together with 390 mg of isomer (Z) which is recrystallized in the same way, m.p. 266° C.

Isomer (E):

IR Spectrum (CHCl₃):

|  | cm⁻ | cm⁻¹ | cm⁻¹ |
| --- | --- | --- | --- |
| OH (oxime) | 3,585 (+combined) | | |
| conjugated system + aromatic C—O—C | 1,613 (max) 1,544 and 1,081 and | 1,592 (shoulder) 1,491 1,040 | |

Analysis: C₂₈H₃₃NO₂S 447.64:

|  | C% | H% | N% | S% |
| --- | --- | --- | --- | --- |
| Calculated | 75.13 | 7.43 | 3.13 | 7.16 |
| Found Isomer (Z) | 75.0 | 7.5 | 3.1 | 7.1 |

IR Spectrum (CHCl₃):

|  | cm⁻¹ | cm⁻¹ | cm⁻¹ |
| --- | --- | --- | --- |
| OH (oxime) | 3,589 (+combined) | | |
| conjugated system + aromatic C—O—C | 1,612 (max) 1,555(f) and 1,081 and | 1,598 1,492(F) 1,040 | |

Analysis:

| | C% | H% | N% | S% |
|---|---|---|---|---|
| Found | 74.9 | 7.3 | 2.9 | 7.0 |

EXAMPLE 31

(17R)
4'5'-dihydro-9-alpha,10-alpha-epoxy-11-beta-4-(3-methylbutyl)sulphonyl]phenyl-spiro(estr-4-en-17,2'-(3H)-furan)-3-one 0.8 g of the product obtained in example 25 is dissolved in 20 cm$^3$ of methylene chloride, cooled to 0° C., then 1.64 g of metachloroperbenzoic acid is added in small fractions, with agitation for 1 hour. A 0.2N solution of sodium thiosulphate is added with agitation for 5 minutes, then the reactional medium is poured into a saturated aqueous solution of sodium bicarbonate and extracted with methylene chloride. The organic phase is washed with water and dried, and the solvents are eliminated under reduced pressure. 0.980 g of the expected product is obtained, which is crystallized from a mixture of methylene chloride and isopropyl ether. m.p. 203° C.

IR Spectrum (CHCl$_3$):

| | cm$^{-1}$ | cm$^{-1}$ | cm$^{-1}$ |
|---|---|---|---|
| $>$C=O | 1,669 (F) | | |
| —C=C aromatic | 1,620 | 1,597 | 1,492 |
| SO$_2$ | 1,317 to 1,144 | | |

Analysis: C$_{32}$H$_{42}$O$_5$S 538.75:

| | C% | H% | S% |
|---|---|---|---|
| Calculated | 71.34 | 7.85 | 5.95 |
| Found | 71.2 | 7.9 | 5.7 |

EXAMPLE 32

(17R)
4-[3-oxo-spiro(estra-4,9-diene-17,2'-(5H)-furan-11-beta-yl]benzoate of 2-amino-2-methylpropyl 4.32 g of (17R) 11-beta-(4-(4,5-dihydro-4,4-dimethyl-2-oxazolyl)phenyl]-spiro(estra-4,9-dien-17,2'-(5H)-furan)-3-one, prepared as in example 19, is dissolved in 40 cm$^3$ of dioxan and 40 cm$^3$ of 2N hydrochloric acid, heated for three-and-a-half hours at 60° C., then cooled. The reactional medium is poured into an iced aqueous solution of sodium bicarbonate and extracted with methylene chloride. The extracts are washed with water, dried and the solvents are eliminated under reduced pressure.

4.6 g of crude product is recovered, which is chromatographed on silica (eluent, ethyl acetate, then ethyl acetate with triethylamine, 9-1) After crystallization from ether, then from ethyl acetate, 2.54 g of the expected product is obtained, m.p. 178° C.

IR Spectrum (CHCl$_3$):

| | cm$^{-1}$ | cm$^{-1}$ | cm$^{-1}$ |
|---|---|---|---|
| conjugated ester | 1,715 | | |
| ketone at position 3 | 1,658 | | |
| C=C aromatic | 1,608 | 1,569 (shoulder) | |
| NH$_2$(def.) | | | 1,504 |

Analysis: C$_{32}$H$_{39}$NO$_4$ 501.67:

| | C% | H% | N% |
|---|---|---|---|
| Calculated | 76.61 | 7.83 | 2.79 |
| Found | 76.3 | 7.7 | 2.6 |

EXAMPLE 33

Ethyl (17R)
4-[3-oxo-spiro(estra-4,9-diene-17,2'-(3H)furan-11-beta-yl]benzoate and (17R)
4-[3-oxo-spiro(estra-4,9-diene-17,2'-(3H)-furan-11-beta-yl]-N-2-hydroxy-(1,1-dimethylethyl) benzamide At ambient temperature and under an inert atmosphere, 2.06 g of the product prepared in example 32 is agitated for 2 hours in suspension in 50 cm$^3$ of ethanol and 8 cm$^3$ of a 0.7M solution in ethanol of sodium ethylate.

The suspension is poured into an iced aqueous solution of hydrochloric acid and extracted with methylene chloride. The organic phase is washed and dried and the solvents are eliminated under reduced pressure. The residue is chromatographed on silica (eluent: cyclohexane and ethyl acetate 7-3, then ethyl acetate and triethylamine 9-1 and 6-4).

There are obtained:
1.375 g of the product expected in the form of ethyl benzoate (product A), which is recrystallized from ether, then from ethanol, m.p. 140° C. then 182° C., and
0.385 g of the expected product N-2-hydroxy-(1,1-dimethylethyl) benzamide, (product B), which is recrystallized from ether, then from isopropanol, m.p. 147° to 157° C.

IR Spectrum of the product A (CHCl$_3$):

| | cm$^{-1}$ | cm$^{-1}$ | cm$^{-1}$ |
|---|---|---|---|
| conjugated ester | 1,711 | | |
| dienone | 1,658 | | |
| C=C aromatic | 1,608 | 1,570 | 1,503 |

IR Spectrum of the product B (CHCl$_3$):

| | cm$^{-1}$ | cm$^{-1}$ | cm$^{-1}$ |
|---|---|---|---|
| secondary amide, NH | 3,430 | | |
| amide II | 1,526 | | |
| amide + C=O dienone | 1,655 | | |
| C=C dienone | 1,607 | | |
| aromatic | 1,566 | to | 1,498 |
| OH about | 3,618 | | |

EXAMPLE 34

(17)

4-[spiro-(3-oxo-estra-4,9-diene-17,2'-(5H)-furan)-11-beta-yl]benzoic acid

A suspension of 0.3 g of the product A obtained in example 33 in 3 cm³ of ethanol is swept with nitrogen for 20 minutes, then 1 cm³ of an (N) aqueous solution of sodium hydroxide is added. The suspension is heated for one-and-a-half hours at 60° C., then cooled and poured into a dilute solution of hydrochloric acid. After extracting with ethyl acetate, the organic phase is washed with water, dried, the solvents are eliminated under reduced pressure, and 0.250 g of crude product is obtained, which is purified by chromatography on silica (eluent: ethyl acetate). m.p. about 170° C.

EXAMPLE 35

(17R)

13-beta-ethyl-11-beta-[4-(methylthio)-phenyl]spiro(-gona-4,9-dien-17,2'-(5H)-furan-3-one

Stage A: (1,2-ethanediyl) cyclic acetal of 5-alpha,10-alpha-epoxy-13-beta-ethyl-gona-9(11)-en-3,17-dione At ambient temperature, 21.3 g of hexafluoroacetone sesquihydrate is added to a solution of 21.36 g of (1,2-ethanediyl) cyclic acetal of 13-beta-ethyl-gon-5(10),9(11)-en-17-one in 213 cm³ of methylene chloride, cooled to 0°/+5° C., and, over 5 minutes, 42.7 cm³ of hydrogen peroxide is added, with agitation for 2 hours 15 minutes under an inert atmosphere. Sodium thiosulphate is added, and extraction is done with methylene chloride. The extracts are washed and dried and the solvents are eliminated under reduced pressure. 26.41 g of the expected product is obtained.

IR Spectrum (CHCl₃):

|  | cm⁻¹ |
|---|---|
| C=O | 1,730 |
| CH₂ in position 16, | 1,406 |
| C=C | 1,640 |

Stage B: (Z) 3,3-(1,2ethanediyl) cyclic acetal of 5-alpha,10-alphaepoxy-13-beta-ethyl-17-beta-hydroxy-17-alpha-[3-(1-tetrahydro-2H-2-pyrannyloxy)-1-propynyl]-gon-9(11)-en-3,17-dione The operation is done as in stage A of example 5, starting with 19.9 g of the product obtained above and 14.6 cm³ of the reagent HC≡C—CH₂OTHP and allowing to react for 15 hours at ambient temperature. 33.533 g of crude product is obtained, which is chromatographed on silica (eluent: methylene chloride - ethyl acetate, 9-1), and 15.498 g of the expected product is obtained.

IR Spectrum (CHCl₃):

|  | cm⁻¹ |
|---|---|
| OH— | 3.599 |
| —C≡C— | 1,640 |

Stage C: (Z) (1,2-ethanediyl) cyclic acetal of 5-alpha-10-alphaepoxy-13-beta-ethyl-17-beta-hydroxy-17-alpha-[3-(tetrahydro-2H-2-pyrannyloxy)-1-propenyl]-gon-9(11)-en-3-one 15.45 g of the product obtained at stage B in 320 cm³ of ethyl acetate and 3.2 cm³ of pyridine is hydrogenated for 4 hours under a pressure of 1.2 bars in the presence of 154 mg of barium sulphate with 10% of palladium. The catalyst is filtered off and the remainder is washed with ethyl acetate and concentrated to dryness. 14.705 g of crude product is obtained, which is chromatographed on silica (eluent: methylene chloride - ethyl acetate 9-1). 9.819 g of the expected product is recovered.

IR Spectrum (CHCl₃):

|  | cm⁻¹ | cm⁻¹ |
|---|---|---|
| OH | 3,600 (f) + combined | 3,420 |
| —C=C— | 1,640 (f) |  |

Stage D: (Z) (1,2-ethanediyl) cyclic acetal of 5-alpha-17-betadihydroxy-13-beta-ethyl-11-beta-[4-(methylthio)phenyl]-17-alpha-[3-(tetrahydro-2H-2-pyrannyloxy)]-1-propenyl-gon-9(11)-en-3-one The operation is done as in stage B of example 3, starting with 3.5 g of the product obtained in the preceding stage, 178 mg of cuprous chloride and 16.3 cm³ of a solution of parabromothioanisole magnesium compound solution, titrating 1.1 M/1.

After chromatography on silica (eluent: cyclohexane-ethyl acetate, 7-3), 3.46 g of the expected product is obtained IR Spectrum (CHCl₃):

|  | cm⁻¹ | cm⁻¹ |
|---|---|---|
| OH, about aromatic | 3,600 (f) + combined | 3,500 (F) |
| " | 1,592 (f) |  |
| " | 1,556 |  |
| " | 1,492 |  |

Stage E: (Z) 13-beta-ethyl-17-beta-hydroxy-17-alpha-(3-hydroxy-1-propenyl)-11-beta-[4-(methylthio)-phenyl]-gona-4,9-dien-3-one Under an inert atmosphere, 17 cm³ of 2N hydrochloric acid is added to a suspension of 3.4 g of the product obtained in the previous stage in 68 cm³ g of ethanol and agitated for 1 hour 30 minutes at ambient temperature. The reactional medium is then poured on to ice, 5 cm³ of concentrated ammonia is added, followed by washing with water, drying and concentrating to dryness under reduced pressure. 2.961 g of crude product is obtained, which is chromatographed on silica (eluent: cyclohexane-ethyl acetate, 5-5). After crystallization from isopropyl ether, 1.816 g of the expected product is obtained, m.p. 186° C.

IR Spectrum (CHCl₃):

|  | cm⁻¹ | cm⁻¹ | cm⁻¹ |
|---|---|---|---|
| OH | 3,616 |  |  |
| C=O Conjugated | 1,652 (F) |  |  |
| —C=C— | } 1,597 | 1,555 | 1,492 (F) |

-continued

| | cm$^{-1}$ | cm$^{-1}$ | cm$^{-1}$ |
|---|---|---|---|
| aromatic | | | |

Stage F: (17R) 13-beta-ethyl-11-beta-[4-(methylthio)-phenyl]spiro(-gona-4,9-dien-17,2'-(5H)-furan-3-one The operation is done as in stage E of example 3, starting with 1.5 g of the preceding product, 30 cm$^3$ of pyridine, 3 g of tosyl chloride and 180 cm$^3$ of 2N hydrochloric acid. 1.981 g of crude product is obtained, which is chromatographed on silica (eluent: cyclohexane-ethyl acetate 7-3, then 8-2).

IR Spectrum (CHCl$_3$):

| | cm$^{-1}$ | cm$^{-1}$ | cm$^{-1}$ |
|---|---|---|---|
| C=O conjugated | 1,653 | | |
| —C=C— aromatic | 1,598 | 1,556 | 1.491 |

EXAMPLE 36

(17R) 11-beta-[4-[2-(dimethylamino)ethoxy]phenyl]spiro(estra-1,3,5(10)-trien-17,2'-(5H)-furan-3-ol and its acetate

1. Formation of the phenol acetate

The operation is done as in example 28, utilizing at the start 0.250 g of the product obtained in example 20, 0.25 cm$^3$ of acetic anhydride and 0.2 cm$^3$ of acetyl bromide.

After purification by chromatography, 0.150 g of the acetate sought is obtained.

2. Saponification

The operation is done as in example 28, using at the start 70 mg of the acetate obtained above in 1.5 cm$^3$ of methanol with 0.1 cm$^3$ of sodium hydroxide, and 60 mg of the expected product is obtained.

IR Spectrum (CHCl$_3$):

| | cm$^{-1}$ | cm$^{-1}$ | cm$^{-1}$ |
|---|---|---|---|
| OH | 3,600 | | |
| aromatic | 1,610 | 1,581 | 1,512 |
| | 1,086 | | |

By operating in identical ways to those described above, there have also been prepared:

(17R) 4',5'-dihydro-11-beta-[4-[methyl(dimethyl amino ethyl)amino]-phenyl]-spiro(estra-4,9-dien-17,2'-(3H)-furan-3-one, (17R) 4',5'-dihydro-11-beta-[4-[methyl(dimethyl amino ethyl)amino]-phenyl]-spiro(estra-1,3,5(10)-trien-17,2'-(3H)-furan-3-ol, (17S) 4',5'-dihydro-11-beta-[4-(dimethylamino)phenyl]-13-alpha methyl-spiro(gona-4,9-dien-17,2'-(3H)-furan)-3-one.

(17R) 4',5'-dihydro-11-beta-[4-(dimethylamino)phenyl]-13-alpha methyl-spiro(gona-4,9-dien-17,2'-(3H)-furan)-3-one.

Pharmaceutical composition

Tablets have been prepared answering to the following formula:

| | |
|---|---|
| Product of example 4 | 50 mg |
| Excipient (talc, starch, magnesium stearate) q.s. for a tablet finished at | 120 mg. |

PHARMACOLOGICAL STUDY OF THE INVENTION PRODUCTS

1. Study of the activity of the invention products on the hormone receptors

Progestogene receptor of rabbit uterus

Impuberal rabbits weighing about 1 kg receive a cutaneous application of 25 g of estradiol. 5 days after this treatment, the animals are killed, the uterus is removed, weighed and homogenized at 0° C., using a Potter teflon-glass, in a buffered solution TS (tirs 10 mM, saccharose 0.25 M, HCl pH 7.4) (1 g of tissue for 50 ml of TS). The homogenate is then ultra-centrifuged (105,000 g×90 min.) at 0° C.

Aliquots of the supernatant so obtained are incubated at 0° C. for a time t, with a constant concentration (T) of tritiated product R (17,21-dimethyl-19-nor-4,9-pregnadiene-3,20-dione) in the presence of increasing concentrations (0–2500.10$^{-9}$M either of R cold, or of cold progesterone, or of the cold product under test. The concentration (B) of bonded triated (R) is then measured in each incubate by the technique of adsorption on carbon dextran.

Glucocorticoid receptor of the rat thymus

Male Sprague-Dawley EOPS rats, weighing 160 to 200 g are suprerenalectomized. 4 to 8 days after this ablation, the animals are killed, and the thymus is removed and homogenized at 0° C. in a buffer, Tris 10 mM, saccharose 0.25M, dithiothreitol 2 mM, HCl pH 7.4, using a Potter polytetrafluoroethylene-glass (1 g of tissue for 10 ml of TS). The homogenate is then ultra-centrifuged (105,000 g×90 min.) at 0° C. Aliquots of the supernatant so obtained are incubated at 0° C. for a time (t) with a constant concentration (T) of tritiated dexamethasone in the presence of increasing concentrations (0–2,500.10$^{-9}$M) either of cold dexamethasone, or of the cold product under test. The concentration of bonded tritiated dexamethasone (B) is then measured in each incubate by the technique of adsorption on carbon dextran.

Calculation of the relative bonding affinity

The calculation of the relative bonding affinity (RBA) is the same for all the receptors.

The two following curves are drawn: the percentage of bonded tritiated hormone B/T as a function of the concentration of the cold reference hormone, and B/T as a function of the logarithm of the concentration of the cold product under test. The straight line of the equation $$I_{50} = \left(\frac{B}{T}\max + \frac{B}{T}\min\right)/2$$

is determined. B/T max=percentage of tritiated hormone bonded for an incubation of this tritiated hormone at the concentration (T). B/T min=percentage of tritiated hormone bonded for an incubation of this tritiated hormone at the concentration (T) in the presence of a great excess of cold hormone ($2,500.10^{-9}$M).

The intersections of the straight line $I_{50}$ with the curves enables the concentrations of the cold reference hormone (CH) and of the cold product under test (CX) to be evaluated which inhibit by 50% the bonding of the tritiated hormone on the receptor.

The relative bonding affinity (RBA) of the product under test is determined by the equation:

$$ARL = 100\frac{(CH)}{(CX)}$$

The following are the results obtained:

| Products of Examples | Time of incubation at 0° C. | Pro-gestogen 2 H | 24 H | Gluco-corticoid 4 H | 24 H |
|---|---|---|---|---|---|
| 1 | | 62 | 307 | 118 | 48 |
| 2 | | 23 | 222 | 142 | 96 |
| 3 | | 35 | 242 | 56 | 41 |
| 4 | | 78 | 388 | 69 | 39 |

Conclusion

The products studied, particularly the product of example 4, offer a very marked affinity for the glucorticoid and progestogen receptors.

From the results obtained it can be concluded that the products can offer agonist or antagonist activities of the glucocorticoids and of the progestogens, II. Antiglucocorticoid activity The technique used derives from the method described by Dausse et Col. in "Molecular Pharmacology", 13, 948-953, (1977) ("the relationship between glucocorticoid structure and effects upon Thymocytes") for the thymocytes of mice.

The thymocytes of suprarenalectomized rats are incubated at 37° C. for 30 hours in a nutritive medium containing $5.10^{-8}$M of dexamethasone in the presence or not of a product being studied, at different concentrations. Tritiated uridine is added, and the incubation is continued for one hour. The incubates are cooled, and treated with a 5% solution of trichloroacetic acid, then filtered on Whatman GF/A paper, and washed three times with a 5% trichloroacetic acid solution. The radio-activity retained by the filter is determined.

Glucocorticoids and in particular, dexamethasone, cause a reduction in the incorporation of tritiated uridine. The products of examples 1 to 4 oppose this effect.

| Product of the example | $5.10^{-8}$ dexamethasone + product to be tested at a concentration of: | % of inhibition of the effect of the dexamethasone |
|---|---|---|
| 1 | $10^{-8}$M | 11 |
| | $10^{-7}$M | 51 |

-continued

| Product of the example | $5.10^{-8}$ dexamethasone + product to be tested at a concentration of: | % of inhibition of the effect of the dexamethasone |
|---|---|---|
| | $10^{-6}$M | 125 |
| 2 | $10^{-8}$M | 0 |
| | $10^{-7}$M | 18 |
| | $10^{-6}$M | 32 |
| 3 | $10^{-8}$M | 0 |
| | $10^{-7}$M | 12 |
| | $10^{-6}$M | 84 |
| 4 | $10^{-8}$M | 0 |
| | $10^{-7}$M | 21 |
| | $10^{-6}$M | 80 |

It has elsewhere been established that the use of the products tested alone does not cause any effect of the glucocorticoid type.

Conclusion

The products studied offer a very marked antiglucocorticoid activity while having no glucocorticoid activity.

III. Abortive activity in rats

The day J1 of gestation is determined by the presence of spermatozoids in the vaginal smear. On day J9 of the gestation, the product is administered in suspension in carboxymethyl cellulose containing 0.5% of Tween.

The animals are killed 72 hours after the treatment and the uterus is examined to determine the state of gestation.

A complete abortion was found in all the animals of the group with the products of examples 1 to 4, administered at a dose of 3 mg/kg.

We claim:

1. A compound selected from the group consisting of a compound of the formula

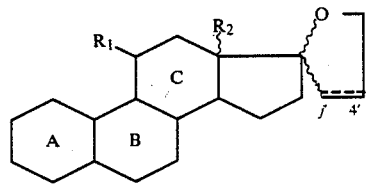

wherein $R_1$ is selected from the group consisting of carbocyclic aryl, heterocyclic aryl and aralkyl, all unsubstituted or substituted except alkynylphenyl with at least one member selected from the group consisting of alkyl and alkoxy of 1 to 8 carbon atoms, alkenyloxy of 2 to 8 carbon atoms, alkyl, alkenyl and alkynyl of up to 8 carbon atoms substituted with at least one member of the group consisting of halogen, —OH, —CF$_3$, acyl of 1 to 6 carbon atoms, carboxy, esterified carboxy, alkylthio and oxidized alkylthio of 1 to 8 carbon atoms, —NH$_2$, mono and dialkylamino, the alkyls having 1 to 8 carbon atoms and oxidized amino, mono and dialkylamino, substituted mono or dialkylamino and a unsubstituted or substituted nitrogen heterocycle which may contain —O— or —N— or —S— in the ring, $R_2$ is either $\alpha'$ or $\beta$ hydrocarbon of 1 to 18 carbon atoms, the wavy line of the spiro ether indicates the oxygen may be a $\alpha$- or $\beta$-, the dotted line in the 3',4'-position indicates the absence or presence of a double bond, the A and B rings are selected from the group consisting of

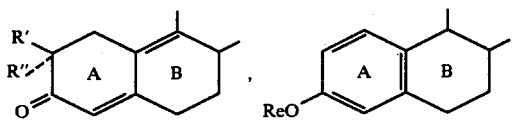 , 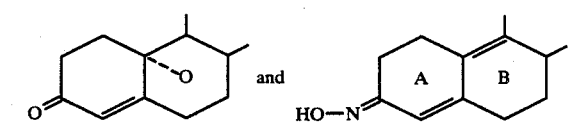 ,

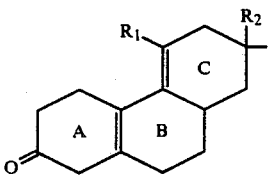 and 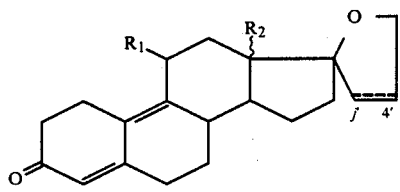

wherein R' and R" are individually selected from the group consisting of hydrogen and alkyl of 1 to 4 carbon atoms, Re is selected from the group consisting of hydrogen, alkyl of 1 to 6 carbon atoms and acyl or the A,B and C rings may be

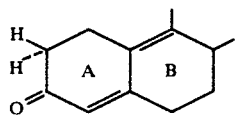

and their non-toxic, pharmaceutically acceptable salts.

2. A compound of claim 1, selected from the group consisting of a compound of the formula

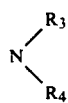

wherein $R_1$ and $R_2$ and the dotted line have the definition of claim 1 and the oxygen of the spiro ether is in the β-position and their non-toxic, pharmaceutically acceptable salts.

3. A compound of claim 1 wherein the oxygen of the spiro ether is in the β-position and the A and B rings are

[structure]

4. A compound of claim 1 wherein $R_1$ is selected from the group consisting of aryl and aralkyl substituted with

[structure with $R_3$, N, $R_4$]

an aryl substituted with CH$_3$S— or CH$_3$—CH$_2$—S—, $R_3$ and $R_4$ are individually primary, secondary or tertiary alkyl of 1 to 8 carbon atoms or taken together with the nitrogen atom form a heterocycle containing or not a heteroatom selected from the group consisting of oxygen, nitrogen, sulfur and silicium.

5. A compound of claim 1 wherein $R_1$ is phenyl unsubstituted or substituted in the p-position.

6. A compound of claim 1 wherein $R_1$ is selected from the group consisting of

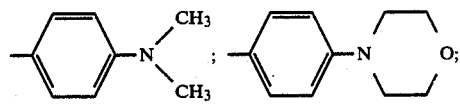

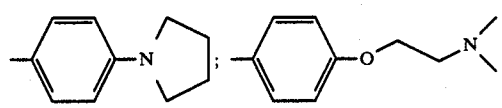

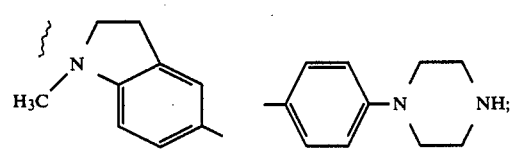

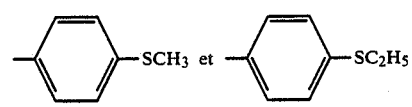

7. A compound of claim 6 wherein $R_1$ is

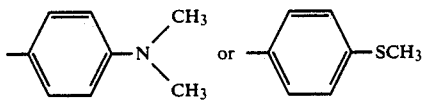

8. A compound of claim 1 wherein $R_2$ is selected from the group consisting of α-methyl, β-methyl and β-ethyl.

9. A compound of claim 1 selected from the group consisting of (17 R) 4',5'-dihydro-11β-[4-(dimethylamino)-phenyl]-spiro-Δ$^{4,9}$-estradien-17,2'-(3H)-furan)-3-one, (17 R) 11β-[4-(dimethylamino)-phenyl]-spiro-Δ$^{4,9}$-estradien-17,2'-(5H)-furan)-3-one, (17 R) 11β-[4-(methylthio)-phenyl]-spiro-Δ$^{4,9}$-estradien-17,2'-(5H)-furan)-3-one, (17 R) 4',5'-dihydro-11β-[4-(methylthio)-phenyl]-spiro-Δ$^{4,9}$-estradien-17,2'-(5H)-furan)-3-one, (17 R) 11β-[4-(1-pyrrolidinyl)-phenyl]-spiro-Δ$^{4,9}$-estradien-17,2'-(5H)-furan)-3-one, (17 R) 4',5'-dihydro-11β-[4-(1-pyrrolidinyl)-phenyl]-spiro-Δ$^{4,9}$-estradien-17,2'-(3H)-furan)-3-one, (17 R) 4',5'-dihydro-11β-[4-(2,3-dihydro-1-methyl)-(1H)-indol-5-yl]-spiro-Δ$^{4,9}$-estradien-17,2'-(3H)-furan)-3-one, (17 R) 11β-[4-(ethylthio)-phenyl]-spiro-Δ$^{4,9}$-estradien-17,2'-(5H)-furan)-3-one and their non-toxic, pharmaceutically acceptable salts.

10. A compound of the formula

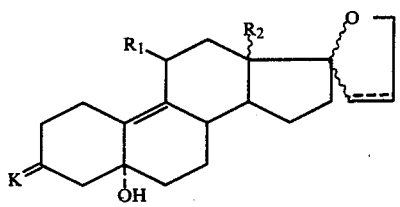

wherein $R_1$ and $R_2$ have the definition of claim 1 and K is a ketone protective group.

11. An antiprogestomimetic composition comprising an antiprogestomimetically effective amount of at least one compound of claim 1 and an inert pharmaceutical carrier.

12. A compound of claim 11, selected from the group consisting a compound of the formula

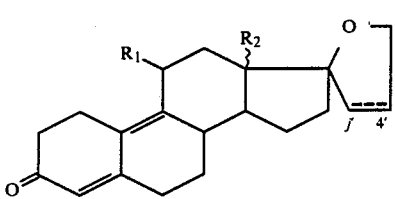

wherein $R_1$ and $R_2$ and the dotted line have the definition of claim 1 and the oxygen of the spiro ether is in the β-position and their non-toxic, pharmaceutically acceptable salts.

13. A composition of claim 11 wherein in the formula of the compound, the oxygen of the spiro ether is in the β-position and the A and B rings are

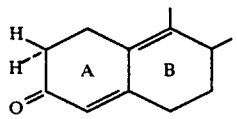

14. A composition of claim 11 wherein in the formula of the compound, $R_1$ is selected from the group consisting of aryl and aralkyl substituted with

and aryl substituted with $CH_3S—$ or $CH_3—CH_2—S—$, $R_3$ and $R_4$ are individually primary, secondary or tertiary alkyl of 1 to 8 carbon atoms or taken together with the nitrogen atom form a heterocycle containing or not a heteroatom selected from the group consisting of oxygen, nitrogen, sulfur and silicium.

15. A composition of claim 11 wherein in the formula of the compound $R_1$ is phenyl unsubstituted or substituted in the p-position.

16. A composition of claim 11 wherein, in the formula of the compound, $R_1$ is selected from the group consisting of

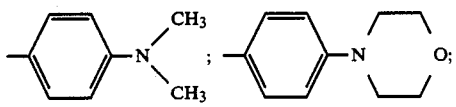

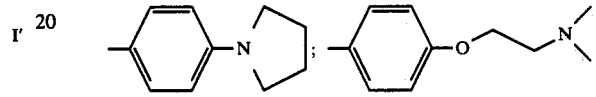

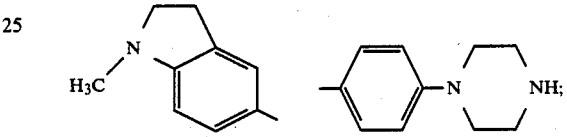

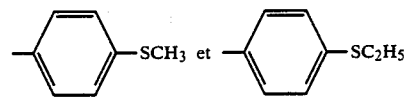

17. A composition of claim 11 wherein, in the formula of the compound, $R_1$ is

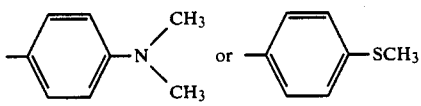

18. A composition of claim 11 wherein, in the formula of the compound, $R_2$ is selected from the group consisting of α-methyl, β-methyl and β-ethyl.

19. A method of inducing contraception or interruption of pregnancy in warm-blooded animals comprising administering to female warm-blooded animals a sufficient amount of at least one compound of claim 1 to interrupt pregnancy or to induce contraception.

* * * * *